US012422435B2

United States Patent
Shanmugam et al.

(10) Patent No.: US 12,422,435 B2
(45) Date of Patent: Sep. 23, 2025

(54) METHODS AND SYSTEMS FOR EVALUATION OF IMMUNE CELL INFILTRATE IN STAGE III COLORECTAL CANCER

(71) Applicants: Ventana Medical Systems, Inc., Tucson, AZ (US); Mayo Foundation for Medical Education and Research, Rochester, MN (US)

(72) Inventors: Kandavel Shanmugam, Oro Valley, AZ (US); Frank A. Sinicrope, Rochester, MN (US)

(73) Assignees: Ventana Medical Systems, Inc., Tucson, AZ (US); Mayo Foundation for Medical Education and Research, Rochester, MN (US)

( * ) Notice: Subject to any disclaimer, the term of this patent is extended or adjusted under 35 U.S.C. 154(b) by 1362 days.

(21) Appl. No.: 16/945,160

(22) Filed: Jul. 31, 2020

(65) Prior Publication Data

US 2020/0355688 A1    Nov. 12, 2020

Related U.S. Application Data

(63) Continuation of application No. PCT/EP2019/052373, filed on Jan. 31, 2019.
(Continued)

(51) Int. Cl.
*G01N 33/574* (2006.01)
*G06T 7/00* (2017.01)
(Continued)

(52) U.S. Cl.
CPC ..... *G01N 33/57419* (2013.01); *G06T 7/0012* (2013.01); *G06T 7/12* (2017.01);
(Continued)

(58) Field of Classification Search
CPC ... G01N 33/57419; G06T 7/12; G06T 7/0012; G06T 2207/20104; G06T 2207/30024;
(Continued)

(56) References Cited

U.S. PATENT DOCUMENTS 8,481,271 B2   7/2013  Galon et al.
9,298,968 B1   3/2016  Peljto et al.
(Continued)

FOREIGN PATENT DOCUMENTS

EP     1777523 A1    4/2007
WO   2013186374 A1   12/2013
(Continued)

OTHER PUBLICATIONS

Fabienne Hermitte "Biomarkers immune monitoring technology primer: Immunoscore Colon", Journal for Immuno Therapy of Cancer, vol. 232, No. Suppi, Sep. 20, 2016, p. 2 (Year: 2016).*
(Continued)

*Primary Examiner* — John J Lee
(74) *Attorney, Agent, or Firm* — Charney IP Law LLC; Thomas M. Finetti

(57) ABSTRACT

Immune context scores are calculated for stage III colorectal tumor tissue samples using continuous scoring functions. Feature metrics for at least one immune cell marker are calculated for a region or regions of interest, the feature metrics including at least a density of human CD3+ cells in a region of interest including an invasive margin. A continuous scoring function is then applied to a feature vector, the output of which is an immune context score. The immune context score may then be plotted as a function of a diagnostic or treatment metric, such as a prognostic metric (e.g. overall survival, disease-specific survival, progression-free survival) or a predictive metric (e.g. likelihood of response to a particular treatment course). The immune
(Continued)

context score may then be incorporated into diagnostic and/or treatment decisions.

46 Claims, 4 Drawing Sheets

Specification includes a Sequence Listing.

Related U.S. Application Data

(60) Provisional application No. 62/624,649, filed on Jan. 31, 2018.

(51) Int. Cl.
*G06T 7/12* (2017.01)
*G16H 10/40* (2018.01)
*G16H 10/60* (2018.01)
*G16H 20/10* (2018.01)
*G16H 30/40* (2018.01)
*G16H 50/20* (2018.01)
*G16H 50/30* (2018.01)

(52) U.S. Cl.
CPC .............. *G16H 10/40* (2018.01); *G16H 10/60* (2018.01); *G16H 20/10* (2018.01); *G16H 30/40* (2018.01); *G16H 50/20* (2018.01); *G16H 50/30* (2018.01); *G06T 2207/20104* (2013.01); *G06T 2207/30024* (2013.01); *G06T 2207/30028* (2013.01)

(58) Field of Classification Search
CPC .......... G06T 2207/30028; G16H 10/40; G16H 10/60; G16H 50/30; G16H 50/20; G16H 20/10; G16H 30/40
See application file for complete search history.

(56) References Cited

U.S. PATENT DOCUMENTS

| | | | |
|---|---|---|---|
| 11,079,382 | B2 | 8/2021 | Sebastiao et al. |
| 2013/0164762 | A1 | 6/2013 | Emile et al. |
| 2013/0310267 | A1* | 11/2013 | Gustavson ....... G01N 33/57415 506/9 |
| 2015/0153349 | A1 | 6/2015 | Galon et al. |
| 2020/0234442 | A1* | 7/2020 | Barnes ................. C12Q 1/6886 |
| 2021/0311060 | A1 | 10/2021 | Barnes et al. |

FOREIGN PATENT DOCUMENTS

| | | |
|---|---|---|
| WO | 2015121465 A1 | 8/2015 |
| WO | 2015124737 A1 | 8/2015 |
| WO | 2015164501 A2 | 10/2015 |
| WO | 2016/077553 A1 | 5/2016 |
| WO | 2017103086 A1 | 6/2017 |
| WO | 2017151755 A1 | 9/2017 |
| WO | 2017194556 A1 | 11/2017 |
| WO | 2019020556 A1 | 1/2019 |

OTHER PUBLICATIONS

Fabienne Hermitte "Biomarkers immune monitoring technology primer: Immunoscore Colon", Journal for InmunoTherapy of Cancer, vol. 4, No. 57, Sep. 20, 2016, pp. 1-3. (Year: 2016).*
International Search Report and Written Opinion of International Patent Application No. PCT/EP2019/052373 dated Jun. 17, 2019.
Kwak, Yoonjin et al., "Immunoscore encompassing CD3+ and CD8+ T Cell densities in distant metastasis is a robust prognostic marker for advanced colorectal cancer", Oncotarget, 2016, pp. 81778-81790, vol. 7, No. 49.
Hermitte, Fabienne, "Biomarkers immune monitoring technology primer: Immunoscore® Colon", Journal for ImmunoTherapy of Cancer, 2016, pp. 1-3, vol. 4, No. 57.
Ward-Hartstonge, KirstenA. et al., "Inclusion of BLIMP-1+ effector regulatory T cells improves the Immunoscore in a cohort of New Zealand colorectal cancer patients: a pilot study", Cancer Immunology, Immunotherapy, 2017, pp. 515-522, vol. 66, No. 4.
Yoon, Harry H. et al., "Intertumoral Heterogeneity of CD3 + and CD8 + T-Cell Densities in the Microenvironment of DNA Mismatch-Repair-Deicient Colon Cancers: Implications for Prognosis", Clinical Cancer Research, Oct. 9, 2018, pp. 125-133, vol. 25, No. 1.
Sarkar, Anindya et al., "A Robust Method for Inter-Marker Whole Slide Registration of Digital Pathology Images Using Lines Based Features", IEEE, 2014, pp. 762-765.
Lorsakul, Auranuch et al., "Validation of Multiplex Immunohistochemistry Assays using Automated Image Analysis", Proc. SPIE 10581, Medical Imaging 2018: Digital Pathology, Mar. 6, 2018, 105810J.
Donnem, T. et al., "Strategies for clinical implementation of TNM-Immunoscore in resected nonsmall-cell lung cancer", Annals of Oncology, 2016, pp. 225-232, vol. 27.
Obeid, Joseph M. et al., "Heterogeneity of CD8+ tumor-infiltrating lymphocytes in non-small-cell lung cancer: impact on patient prognostic assessments and comparison of quantification by different sampling strategies", Cancer Immunol Immunother, 2017, pp. 33-43, vol. 66.
Wen, Ti et al., "A Four-Factor Immunoscore System That Predicts Clinical Outcome for Stage II/III Gastric Cancer", Cancer Immunology Research, Jul. 2017, pp. 524-534, vol. 5, No. 7.
International Search Report and Written Opinion of International Patent Application No. PCT/EP2018/069896 dated Jan. 4, 2019.
Venook, Alan P. et al., "Impact of primary (1 degree) tumor location on overall survival (OS) and progression-free survival (PFS) in patients (pts) with metastatic colorectal cancer (mCRC): Analysis of CALBG/SWOG 80405 (Alliance)", Journal of Clinical Oncology, May 20, 2016, vol. 34, No. 15_suppl.
Venook, A. et al., "Impact of primary tumor location on Overall Survival and Progression Free Survival in patients with metastatic colorectal cancer: Analysis of all RAS wt subgroup on CALGB/SWOG 80405 (Alliance)", Journal of Clinical Oncology, Presentation, 2016.
Lee, Won-Suk et al., "Clinical Impact of Tumor-infiltrating Lymphocytes for Survival in Curatively Resected Stage IV Colon Cancer with Isolated Liver or Lung Metastasis", Annals of Surgical Oncology, 2013, pp. 697-702, vol. 20.
Le, Dung T. et al., "Mismatch repair deficiency predicts response of solid tumors to PD-1 blockade", Science, 2017, Jul. 28, 2017, pp. 409-413, vol. 357.
International Search Report and Written Opinion of International Patent Application No. PCT/EP2020/052737 dated Apr. 30, 2020.
Anitei, Maria-Gabriela et al., "Prognostic and Predictive Values of the Immunoscore in Patients with Rectal Cancer", Clinical Cancer Research, 2014, pp. 1891-1899, vol. 20, Issue 7.
Chen, Jianxu et al., "Automatic Lymphocyte Detection in H&E Images with Deep Neural Networks", arXiv:1612.03217v1 (submitted Dec. 9, 2016; available at https://arxiv.org/abs/1612.03217), pp. 1-11.
Forrest, R. et al., "Comparison of visual and automated assessment of tumour inflammatory infiltrates in patients with colorectal cancer", European Journal of Cancer, 2014, pp. 544-552, vol. 50, Issue 3.
Galon, Jerome et al., Towards the introduction of the 'Immunoscore' in the classification of malignant tumours, Journal of Pathology, 2014, pp. 199-209, vol. 232, Issue 2.
Galon, Jerome et al., Validation of the Immunoscore (IM) as a prognostic marker in stage I/II/III colon cancer: Results of a worldwide consortium-based analysis of 1,336 patients. Powerpoint presentation (2016), pp. 1-29 (available at http://meetinglibrary.asco.org/content/168666-176) ("Galon (2016a)").
Galon, Jerome et al., Validation of the Immunoscore (IM) as a prognostic marker in stage I/II/III colon cancer: Results of a worldwide consortium-based analysis of 1,336 patients., J. Clin. Oncol., vol. 34, suppl. Abstract No. 3500 (2016) pp. 1-2 (available at http://meetinglibrary.asco.org/content/168666-176) ("Galon (2016a)").

(56) References Cited

OTHER PUBLICATIONS

Jass, JR et al., "A new prognostic classification of rectal cancer", The Lancet, Jun. 6, 1987, pp. 1303-1306, vol. 329, Issue 8545.

Jass, JR, "Lymphocytic infiltration and survival in rectal cancer", Journal of Clinical Pathology, 1986, pp. 585-589, vol. 39, Issue 6.

Mei, Z. et al., "Tumour-infiltrating inflammation and prognosis in colorectal cancer: systematic review and meta-analysis", British Journal of Cancer, 2014, pp. 1595-1605, vol. 110.

Pages, F. et al., "Immune infiltration in human tumors: a prognostic factor that should not be ignored", Oncogene, 2010, pp. 1093-1102, vol. 29.

Overman, Michael J. et al., Nivolumab in patients with metastatic DNA mismatch repair deficient or microsatellite instability high colorectal cancer (CheckMate 142): An open label, multicentre, phase 2 study, The Lancet Oncology, vol. 18, pp. 1182-1191, 2017.

Tumeh, Paul C. et al., PD-1 blockade induces responses by inhibiting adaptive immune resistance, Nature, vol. 515, No. 7528, pp. 568-571, 16 pp., 2014.

Anitei Clin Cancer Res 2014 20 7 1891-1899 including Supp Data Tables 1-5.

Eisenhauer J Cancer 2008 45 2 228-247.

El Jabbour J Clin Path 2018 71 1 46-51.

Galon Sci 2006 313 5795 1960-1964.

Llosa Cancer Disc 2015 5 1 43-51.

Narayanian Sci Reports 2019 9 13455.

Pages The Lancet 2018 391 10135 2128-2139.

Sinicrope J Clin Oncol 2013 31 29 3664-3672.

Basile et al. Immunotherapy for colorectal cancer: where are we heading? Expert Opin Biol Ther. Jun. 2017; 17 (6):709-721. (Year:2017).

Kareva I. A Combination of Immune Checkpoint Inhibition with Metronomic Chemotherapy as a Way of Targeting Therapy-Resistant Cancer Cells. Int J Mol Sci. Oct. 13, 2017; 18(10):2134. (Year: 2017).

\* cited by examiner

METHODS AND SYSTEMS FOR EVALUATION OF IMMUNE CELL INFILTRATE IN STAGE III COLORECTAL CANCER

CROSS-REFERENCE TO RELATED APPLICATION

This application is a continuation of International Application Serial Number PCT/EP2019/052373, filed 31 Jan. 2019, which claims priority to U.S. Provisional Application Ser. No. 62/624,649, filed 31 Jan. 2018, each of which is incorporated by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000022-011000_ST25.txt" created on 28 Jun. 2020, and 65,729 bytes in size) is submitted concurrently with the instant application, and the entire contents of the Sequence Listing are incorporated herein by reference.

BACKGROUND OF THE INVENTION

Field of the Invention

The invention relates to detection, characterization and enumeration of discrete populations of immune cells in tumor samples for use in prognosing and treating proliferative diseases, such as colorectal cancers.

Description of Related Art

The presence or absence of an inflammatory response is known to be a prognostic factor in a number of different cancer types, including colorectal cancer, melanoma, breast cancer, ovarian cancer, non-Hodgkin's lymphoma, head and neck cancer, non-small-cell lung cancer (NSCLC), esophageal cancer, and urothelial carcinoma, among others. See Pagès et al. (2010). In colorectal cancer, for example, the relative amount of immune cell infiltrate has been considered an independent prognostic factor for colorectal cancers since at least 1986. See Jass (1986). Since then, many groups have evaluated analytical and statistical methods for understanding the interaction between tumor prognosis and its immune context. See Mei et al. (2014) (conducting a meta-analysis of numerous prior studies in colorectal cancers).

In colorectal tumors, three methods of scoring the immune context have predominated:
(1) the Jass score, in which the tumor is graded according to whether there is extensive or little/absent peritumoral lymphocyte infiltrate (see Jass (1987));
(2) Klintrup-Mäkinen grade, in which overall inflammatory cell reaction is scored in hematoxylin and eosin (H&E)-stained slides at the invasive margin (IM) on either a 3-point scale (0=no increase of inflammatory cells at IM; 1=mild and patchy increase of inflammatory cells at IM without destruction of invading cancer cell islets; 2=a band-like infiltrate at the IM with some destruction of cancer cell islets; and 3=very prominent inflammatory reaction, forming a cup-like zone at the invasive margin, and destruction of cancer cell islets); or a 2-point scale (low grade inflammation (scores 0-1 as described above) or high grade inflammation (scores 2-3 as described above), see Galon et al. (2014); and
(3) Galon IMMUNOSCORE, in which slides are immunohistochemically stained for at least two lymphocyte populations (CD3/CD45RO, CD3/CD8 or CD8/CD45RO), and cell densities are separately scored in the tumor core (TC) and IM on a 2 point scale (0=low; 1=high), which scores are then integrated into a composite score from 0 (e.g., CD3 TC low, CD3 IM low, CD8 TC low, CD8 IM low) to 4 (e.g., CD3 TC high, CD3 IM high, CD8 TC high, CD8 IM high) (see Galon et al (2014); Galon (2016a); Galon (2016b); U.S. Pat. No. 8,481,271).

These approaches are not quantitative, but instead use binary scoring systems based on gross observations of relative quantities.

Some attempts have been made to automate such scoring of the immune context.

For example, the IMMUNOSCORE from HalioDx is implemented on an automated digital pathology platform from Definiens. TC and IM regions are separately annotated in an H&E image, which is registered to images of serial sections immunohistochemically stained for CD3 and CD8. The software overlays a 0.8 mm tile in each region, calculates a cell density for each tile within the region, and then reports the density for the entire region as a mean of the three most infiltrated tiles of the region. See Anitei et al. (2014). "High" and "low" scores are determined by defining a cutpoint in mean cell density using a minimum P value approach. Id.

U.S. Pat. No. 9,298,968 describes a cell analysis system that: (1) digitizes stained tissue sections; (2) extracts cell features; (3) stratifies the tissue into separate compartments containing tumor cells or other relevant cell types based on the extracted features; (4) detects and characterizes cells within compartments of interest that stain above a defined threshold level for an inflammatory cell type marker; (5) derives an immune system state score for the tissue section based on the values or statistics of inflammatory cell type markers; and (6) uses the score to stratify patients. Although the '968 patent contemplates the necessity of a cutoff definition and scoring system, it does not appear to provide a concrete methodology for defining such a cutoff or implementing a scoring system. Rather, common approaches such as delineating between "positive" and "negative" regions and applying qualitative histological scoring grades based on intensity (such as 0, 1+, 2+, and 3+) are mentioned without explication for how such scoring systems could be integrated into a useful prognostic score. Therefore, the '968 Patent only describes, at an aspirational level, a system that might be useful for automating analysis, but does not describe any specific prognostic analyses.

Forrest et al. (2014) propose an automated method of calculating a Klintrup-Mäkinen grade using the SLIDE-PATH Tissue Image Analysis Version 2.0 software from Leica Biosystems. The invasive margin is annotated in H&E sections and immune cell densities (expressed as nuclei/$mm^2$) are automatically detected in the annotated regions on the basis of staining intensities, cell size and size of nuclei. Three serial sections for each tumor are tested and the cell density is expressed as the mean of the three sections. The mean cell densities are then assigned a grade of 0, 1, 2, or 3 based on the quartile in which the mean density falls, or in a category of "weak" (Grades 0 and 1) or "strong" (grades 2 and 3).

Each of the foregoing methods, whether automated or manual, relies on a binary scoring system in which a wide variety of potential cell counts are binned together and considered to be effectively the same. While such an approach can make manual analysis and score computation relatively easy, it does so at the expense of the accuracy of the prognosis. Thus, each method could result in misprognosis and/or missed opportunity for selection of an effective treatment for many patients.

BRIEF SUMMARY OF THE INVENTION

This disclosure relates generally to the quantitative assessment of immune cells in stage III colorectal tumors including, for example, T-lymphocytes (immune cells positive for the CD3 biomarker), using a continuous scoring function to calculate an immune context score (ICS) for a sample of the tumor.

In an embodiment, a method is provided comprising: (a) annotating a region of interest (ROI) on a digital image of a tumor tissue section; (b) calculating a feature vector including a feature metric comprising a quantitative measure of CD3+ cells in the ROI; and (c) applying a continuous scoring function to the feature vector to calculate an immune context score for the tissue section. In an embodiment, one or more types of immune cells are detected morphologically (such as in an image of a sample stained with hematoxylin and eosin) and/or on the basis of cells expression of one or more immune cell markers. In an embodiment, the continuous scoring function is a non-linear time-to-event function, such as a function derived from a Cox proportional hazard model. In an exemplary embodiment the "time to event" is selected from the group consisting of disease-free survival, progression free survival, and overall survival.

In another embodiment, a computer-implemented method is provided comprising causing a computer processor to execute a set of computer-executable functions stored on a memory, the set of computer-executable functions comprising: (A) obtaining a digital image of a tissue section of a stage III colorectal tumor, wherein the tissue section is histochemically stained for at least human CD3; (B) annotating one or more regions of interest (ROI) in the digital image, the ROI comprising an invasive margin (IM) of the tumor; and (C) applying a scoring function to the ROI, wherein the scoring function comprises: (C1) calculating a feature vector comprising a density of CD3+ cells in the IM; and (C2) applying a continuous scoring function to the feature vector to obtain an immune context score for the tissue section. In one specific embodiment, the continuous scoring function is applied to a feature vector consisting of a density of CD3+ cells in the invasive margin of the tissue section. In some embodiments, the CD3+ density is obtained as a total metric. In other embodiments, the CD3+ density is obtained as a mean or median of a plurality of control regions of the ROI. In some embodiments, the CD3+ density is normalized by applying a normalization factor to the CD3+ density, the normalization factor being equal to a pre-determined upper limit or lower limit of the feature metric. In an embodiment, the normalization factor is obtained by evaluating a distribution of CD3+ densities across a representative population of samples, identifying a skew in the distribution of feature metric values, and identifying a value at which a pre-determined number of samples fall beyond, wherein the value is selected as the normalization factor.

In another specific embodiment, a method is provided comprising: (a) annotating a one or more region(s) of interest (ROI) on a digital image of a tumor tissue section, wherein at least one of the ROIs includes at least a portion of an invasive margin (IM) region; (b) detecting and quantitating cells expressing human CD3 in the ROI; (c) detecting and quantitating cells expressing human CD8 in the ROI; (d) calculating a density of CD3+ cells within the ROI, and optionally normalizing the CD3+ cell density or lymphocyte cell density; and (e) applying a continuous scoring function to the feature vector to obtain an immune context score (ICS) for the tumor. In an embodiment, the at least one ROI including a portion of an IM region is an IM ROI or a peri-tumoral (PT) ROI. In an embodiment, the densities are area cell densities or linear cell densities.

Also provided herein are systems for scoring an immune context of a tumor tissue sample, the systems including at least a computer processor and a memory, wherein the memory stores a set computer executable instructions to be executed by the computer processor, the set of computer executable instructions including any of the processes and methods described herein. In some embodiments, the systems include automated slide stainers for histochemically labelling sections of the tumor tissue sample, and/or means for generating digital images of the histochemically stained sections, such as microscopes operably linked to digital cameras or scanner systems. In further embodiments, the systems may further include a laboratory information system (LIS) for tracking and/or controlling processes to be performed on the samples, sections, and digital images.

Further disclosed and proposed herein are computer programs comprising instructions which, when the program is executed by a computer or a computer network, cause the computer or computer network to carry out the method according to the present invention in one or more of the embodiments enclosed herein when the program is executed on a computer or computer network. Specifically, the computer program may be stored on a computer-readable data carrier, e.g. a non-volatile data carrier. Thus, specifically, one, more than one or even all of method steps (a) to (d) of claim 1, method steps (a) to (c) of claim 5, or method steps (a) to (c) of claim 24 may be performed by using a computer or a computer network, preferably by using a computer program.

Further disclosed and proposed herein is a computer program product having program code means, in order to perform the method according to the present invention in one or more of the embodiments enclosed herein when the program is executed on a computer or computer network. Specifically, the program code means may be stored on a computer-readable data carrier.

Further disclosed and proposed herein is a data carrier having a data structure stored thereon, which, after loading into a computer or computer network, such as into a working memory or main memory of the computer or computer network, may execute the method according to one or more of the embodiments disclosed herein.

Further disclosed and proposed herein is a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed herein is a data processing apparatus comprising means for carrying out the method according to one or more of the embodiments disclosed herein. The data processing apparatus may be or may comprise at least one processor. The term "processor" as used herein is a broad term and is to be given its ordinary and customary meaning to a person of ordinary skill in the art and is not to be limited to a special or customized meaning. The term specifically may refer, without limitation, to an arbitrary electronic device configured for performing one or more operations, specifically logical operations, and/or for executing one or more algorithms or data processing operations. The processor specifically may be or may comprise at least one electronic circuit which is configured for performing operations on one or more external data sources, such as on a memory or a data stream. The processor may comprise at least one integrated circuit configured for performing logical operations. The processor may also comprise at least one application-specific integrated circuit (ASIC) and/or at least one field-programmable gate array (FPGA).

Finally, disclosed and proposed herein is a modulated data signal which contains instructions readable by a computer system or computer network, for performing the method according to one or more of the embodiments disclosed herein.

Referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

DETAILED DESCRIPTION OF THE INVENTION

I. Definitions

Figure 1:
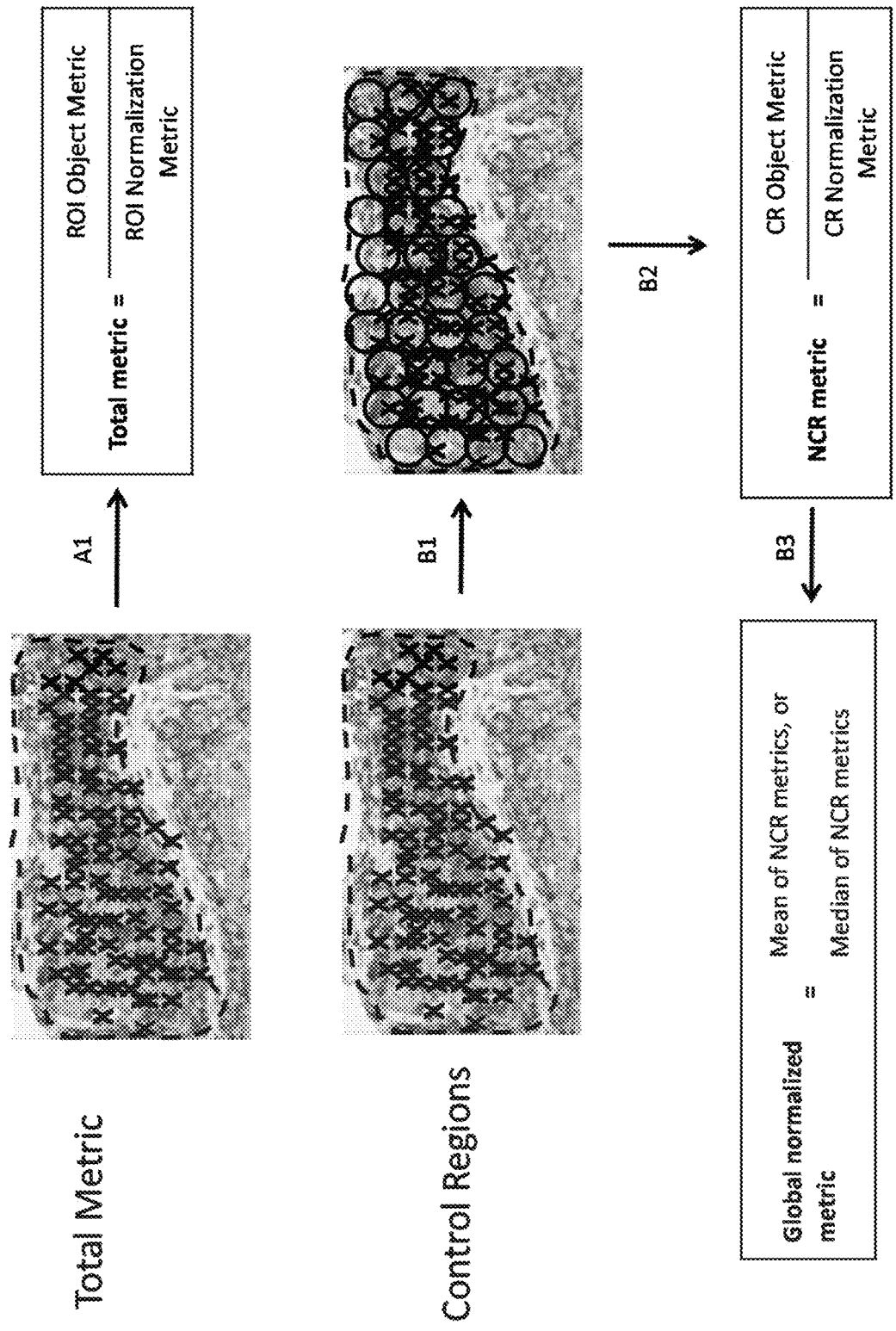
FIG. 1 illustrates two different methods of calculating feature metrics for ROIs. Dashed line in the images illustrates the boundary of an ROI. "X"s in the image indicate objects of interest marked in the image. Circles in the image are control regions that may be used to calculate global metrics for the control region.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

Antibody: The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody fragment: An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Biomarker: As used herein, the term "biomarker" shall refer to any molecule or group of molecules found in a biological sample that can be used to characterize the biological sample or a subject from which the biological sample is obtained. For example, a biomarker may be a molecule or group of molecules whose presence, absence, or relative abundance is:

characteristic of a particular cell or tissue type or state;
characteristic of a particular pathological condition or state; or
indicative of the severity of a pathological condition, the likelihood of progression or regression of the pathological condition, and/or the likelihood that the pathological condition will respond to a particular treatment.

As another example, the biomarker may be a cell type or a microorganism (such as a bacteria, mycobacteria, fungi, viruses, and the like), or a substituent molecule or group of molecules thereof.

Biomarker-specific reagent: A specific detection reagent that is capable of specifically binding directly to one or more biomarkers in the cellular sample, such as a primary antibody.

Cellular sample: As used herein, the term "cellular sample" refers to any sample containing intact cells, such as cell cultures, bodily fluid samples or surgical specimens taken for pathological, histological, or cytological interpretation.

Continuous scoring function: A "continuous scoring function" is a mathematical formula into which the actual magnitude for one or more variables is input (optionally subject to upper and/or lower limits on the value and/or application of a normalization factor). In some examples, the value input into the continuous scoring function is the actual magnitude of the variable. In other examples, the value input into the continuous scoring function is the absolute value of the variable up to (and/or down to, as appropriate) a predetermined cutoff, wherein all absolute values beyond the cutoff value are assigned the cutoff value. In other examples, the value input into the continuous scoring function is a normalized value of the variable. By way of contrast, in a "non-continuous scoring function" (also referred to herein as a "binary scoring function"), each variable is assigned to a pre-determined "bin" (for example, "high," "medium," or "low"), and the same value is input into the mathematical function for all members of the same bin. For example, assume that the variable being assessed is a density of CD3+ T-cells. In a continuous scoring function, the value input into the function is the density of CD3+ T-cells (optionally subject to certain upper- and/or lower-limits and/or normalization). In a non-continuous or binary scoring function, the density value is first analyzed to determine whether it falls into a "high density" or a "low density" bin, and the value that is input into the non-continuous scoring function is whatever arbitrary value is assigned to members of that bin (for example, 0 for low, 1 for high). Thus, consider two samples, a first having a density of 500 CD8+ cells/mm$^2$ and a second having a density of 700 CD8+ cells/mm$^2$. The values input into a continuous scoring function would be 500 and 700, respectively (or modified based upon maximum or minimum cutoff values and/or normalization factor(s)). The values input into a non-continuous scoring function would depend on the bin in which they fall. If the "high bin" encompasses both 500 and 700 cells/mm$^2$, then a value of 1 would be input into the non-continuous scoring function for each sample. If the cutoff between "high" and "low" bins fell somewhere between 500 and 700 cells/mm$^2$, then a value of 0 would be input into a non-continuous scoring function for the first sample, and a value of 1 would be input into a non-continuous scoring function for the second sample. If the "low bin" encompasses both 500 and 700 cells/mm$^2$, then a value of 0 would be input into the non-continuous scoring function for each sample. Please note that these values are intended to illustrate the difference between a continuous scoring function and a non-continuous scoring function, and should not be construed as in any way limiting the scope of the disclosure unless recited in a claim.

Cox proportional hazard model: A model of formula 1:

$$\frac{h(t)}{h_0(t)} = \exp(b_1 X_1 + b_2 X_2 + \ldots b_p X_p) \quad \text{Formula 1}$$

wherein $$\frac{h(t)}{h_0(t)}$$

is the ratio between the expected hazard at time t (h(t)) and a baseline hazard ($h_0(t)$), and $b_1$, $b_2$ . . . $b_p$ are constants extrapolated for each of the independent variables. As used throughout, the ratio $$"\frac{h(t)}{h_0(t)}"$$

will be referred to as the "Cox immune context score" or "$ICS_{cox}$."

Detection reagent: A "detection reagent" is any reagent that is used to deposit a stain in proximity to a biomarker-specific reagent in a cellular sample. Non-limiting examples include biomarker-specific reagents (such as primary antibodies), secondary detection reagents (such as secondary antibodies capable of binding to a primary antibody), tertiary detection reagents (such as tertiary antibodies capable of binding to secondary antibodies), enzymes directly or indirectly associated with the biomarker specific reagent, chemicals reactive with such enzymes to effect deposition of a fluorescent or chromogenic stain, wash reagents used between staining steps, and the like.

Detectable moiety: A molecule or material that can produce a detectable signal (such as visually, electronically or otherwise) that indicates the presence (i.e. qualitative analysis) and/or concentration (i.e. quantitative analysis) of the detectable moiety deposited on a sample. A detectable signal can be generated by any known or yet to be discovered mechanism including absorption, emission and/or scattering of a photon (including radio frequency, microwave frequency, infrared frequency, visible frequency and ultraviolet frequency photons). The term "detectable moiety" includes chromogenic, fluorescent, phosphorescent, and luminescent molecules and materials, catalysts (such as enzymes) that convert one substance into another substance to provide a detectable difference (such as by converting a colorless substance into a colored substance or vice versa, or by producing a precipitate or increasing sample turbidity). In some examples, the detectable moiety is a fluorophore, which belongs to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, OR, ThermoFisher Scientific, 11$^{th}$ Edition. In other embodiments, the detectable moiety is a molecule detectable via brightfield microscopy, such as dyes including diaminobenzidine (DAB), 4-(dimethylamino) azobenzene-4'-sulfonamide (DABSYL), tetramethylrhodamine (DIS- COVERY Purple), N,N'-biscarboxypentyl-5,5'-disulfonato-indo-dicarbocyanine (Cy5), and Rhodamine 110 (Rhodamine).

Feature metric: A value indicative of an expression level of a biomarker in a sample. Examples include: expression intensity (for example, on a 0+, 1+, 2+, 3+ scale), number of cells positive for the biomarker, cell density (for example, number of biomarker-positive cells over an area of an ROI, number of biomarker-positive cells over a linear distance of an edge defining an ROI, and the like), pixel density (i.e. number of biomarker-positive pixels over an area of an ROI, number of biomarker-positive pixels over a linear distance of an edge defining an ROI, and the like), etc. A feature metric can be a total metric or a global metric.

Histochemical detection: A process involving labelling biomarkers or other structures in a tissue sample with biomarker-specific reagents and detection reagents in a manner that permits microscopic detection of the biomarker or other structures in the context of the cross-sectional relationship between the structures of the tissue sample. Examples include immunohistochemistry (IHC), chromogenic in situ hybridization (CISH), fluorescent in situ hybridization (FISH), silver in situ hybridization (SISH), and hematoxylin and eosin (H&E) staining of formalin-fixed, paraffin-embedded tissue sections.

Immune checkpoint-directed therapy: Any therapy that inhibits activation of an immune checkpoint molecule.

Immune checkpoint molecule: A protein expressed by an immune cell whose activation down-regulates a cytotoxic T-cell response. Examples include PD-1, TIM-3, LAG-4, and CTLA-4.

Immune escape biomarker: A biomarker expressed by a tumor cell that helps the tumor avoid a T-cell mediated immune response. Examples of immune escape biomarkers include PD-L1, PD-L2, and IDO.

Invasive margin (IM): The interface between invasive neoplastic tissue and normal tissue. When used in the context of an ROI, "IM" refers to an ROI restricted to a region of a tumor identified by an expert reader as an invasive margin.

Monoclonal antibody: An antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

Non-linear continuous scoring function: A continuous scoring function having the general structure of anything other than f(x)=a+bx, wherein x is a variable and a and b are constants. Thus, for example, "non-linear continuous scoring function" includes non-linear algebraic functions (such as non-constant, non-linear polynomial functions; rational functions; and nth root functions) and transcendental functions (such as exponential functions, hyperbolic functions, logarithmic functions, and power functions).

Normalize: To adjust a feature metric by a fixed factor so that different feature metrics are expressed on the same scale.

Normalization factor: A fixed factor applied to a feature metric to obtain a normalized feature metric.

Normalized feature metric: A feature metric, the value of which has been adjusted by a normalization factor.

Peri-tumoral (PT) region: The region of a tumor in the immediate vicinity of the invasive margin, which may also include a portion of the extra-tumoral tissue and a portion of the tumor core.

Peri-tumoral (PT) ROI: An ROI including at least a portion of the IM region, and optionally extra-tumoral tissue in the immediate vicinity of the IM region and/or a portion of the tumor core region in the immediate vicinity of the IM. For example, "PT ROI" may encompass all pixels within a defined distance of any point on the interface between tumor cells and non-tumor cells, or it may encompass an ROI of a defined width centered on the interface between tumor cells and non-tumor cells, or it may encompass a plurality of defined shapes each centered at a point on the interface between tumor cells and non-tumor cells (such as a plurality of overlapping circles, each centered at a discrete point on the interface between tumor cells and non-tumor cells).

Sample: As used herein, the term "sample" shall refer to any material obtained from a subject capable of being tested for the presence or absence of a biomarker.

Secondary detection reagent: A specific detection reagent capable of specifically binding to a biomarker-specific reagent.

Section: When used as a noun, a thin slice of a tissue sample suitable for microscopic analysis, typically cut using a microtome. When used as a verb, the process of generating a section.

Serial section: As used herein, the term "serial section" shall refer to any one of a series of sections cut in sequence by a microtome from a tissue sample. For two sections to be considered "serial sections" of one another, they do not necessarily need to be consecutive sections from the tissue, but they should generally contain sufficiently similar tissue structures in the same spatial relationship, such that the structures can be matched to one another after histological staining.

Specific detection reagent: Any composition of matter that is capable of specifically binding to a target chemical structure in the context of a cellular sample. As used herein, the phrase "specific binding," "specifically binds to," or "specific for" or other similar iterations refers to measurable and reproducible interactions between a target and a specific detection reagent, which is determinative of the presence of the target in the presence of a heterogeneous population of molecules including biological molecules. For example, an antibody that specifically binds to a target is an antibody that binds this target with greater affinity, avidity, more readily, and/or with greater duration than it binds to other targets. In one embodiment, the extent of binding of a specific detection reagent to an unrelated target is less than about 10% of the binding of the antibody to the target as measured, e.g., by a radioimmunoassay (RIA). In certain embodiments, a biomarker-specific reagent that specifically binds to a target has a dissociation constant (Kd) of $\leq 1$ μM, $\leq 100$ nM, $\leq 10$ nM, $\leq 1$ nM, or $\leq 0.1$ nM. In another embodiment, specific binding can include, but does not require exclusive binding.

Exemplary specific detection reagents include nucleic acid probes specific for particular nucleotide sequences; antibodies and antigen binding fragments thereof; and engineered specific binding compositions, including ADNECTINs (scaffold based on 10th FN3 fibronectin; Bristol-Myers-Squibb Co.), AFFIBODYs (scaffold based on Z domain of protein A from *S. aureus*; Affibody AB, Solna, Sweden), AVIMERs (scaffold based on domain A/LDL receptor; Amgen, Thousand Oaks, CA), dAbs (scaffold based on VH or VL antibody domain; GlaxoSmithKline PLC, Cambridge, UK), DARPins (scaffold based on Ankyrin repeat proteins; Molecular Partners AG, Zürich, CH), ANTICALINs (scaffold based on lipocalins; *Pieris* AG, Freising, DE), NANOBODYs (scaffold based on VHH (camelid Ig); Ablynx N/V, Ghent, BE), TRANS-BODYs (scaffold based on Transferrin; Pfizer Inc., New York, NY), SMIPs (Emergent Biosolutions, Inc., Rockville, MD), and TETRANECTINs (scaffold based on C-type lectin domain (CTLD), tetranectin; Borean Pharma A/S, Aarhus, DK). Descriptions of such engineered specific binding structures are reviewed by Wurch et al., *Development of Novel Protein Scaffolds as Alternatives to Whole Antibodies for Imaging and Therapy: Status on Discovery Research and Clinical Validation*, Current Pharmaceutical Biotechnology, Vol. 9, pp. 502-509 (2008), the content of which is incorporated by reference.

Stain: When used as a noun, the term "stain" shall refer to any substance that can be used to visualize specific molecules or structures in a cellular sample for microscopic analysis, including brightfield microscopy, fluorescent microscopy, electron microscopy, and the like. When used as a verb, the term "stain" shall refer to any process that results in deposition of a stain on a cellular sample.

Subject: As used herein, the term "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

Test sample: A tumor sample obtained from a subject having an unknown outcome at the time the sample is obtained.

Time-to-event model: A mathematical model in which the variables are modeled against their ability to predict the likelihood that a defined event will occur by a time t.

Tissue sample: As used herein, the term "tissue sample" shall refer to a cellular sample that preserves the cross-sectional spatial relationship between the cells as they existed within the subject from which the sample was obtained.

Tumor core (TC): The region of an invasive neoplastic lesion that is not the invasive margin. In the context of an ROI, "TC" refers to a portion of a whole tumor region that is neither IM nor excluded from the ROI as an artifact.

Tumor sample: A tissue sample obtained from a tumor.

Whole tumor (WT) region: A portion of a tissue section characterized by one or more contiguous regions composed substantially entirely of invasive neoplastic cells, including both TC and IM regions.

Whole tumor ROI: An ROI limited to a whole tumor region.

II. Biomarker Descriptions

CD3: CD3 is a cell surface receptor complex that is frequently used as a defining biomarker for cells having a T-cell lineage. The CD3 complex is composed of 4 distinct polypeptide chains: CD3-gamma chain, CD3-delta chain, CD3epsilon chain, and CD3-zeta chain. CD3-gamma and CD3-delta each form heterodimers with CD3-epsilon (εγ-homodimer and εδ-heterodimer) while CD3-zeta forms a homodimer (ζζ-homodimer). Functionally, the εγ-homodimer, εδ-heterodimer, and ζζ-homodimer form a signaling complex with T-cell receptor complexes. Exemplary sequences for (and isoforms and variants of) the human CD3-gamma chain, CD3-delta chain, CD3epsilon chain, and CD3-zeta chain can be found at Uniprot Accession Nos. P09693 (the canonical amino acid sequence for which is disclosed herein at SEQ ID NO: 1), P04234 (the canonical amino acid sequence for which is disclosed herein at SEQ ID NO: 2), P07766 (the canonical amino acid sequence for which is disclosed herein at SEQ ID NO: 3), and P20963 (the canonical amino acid sequence for which is disclosed herein at SEQ ID NO: 4), respectively. As used herein, the term "human CD3 protein biomarker" encompasses any CD3-gamma chain, CD3-delta chain, CD3epsilon chain, and CD3-zeta chain polypeptide having a canonical human sequence and natural variants thereof that maintain the function of the canonical sequence; εγ-homodimers, εδ-heterodimers, and ζζ-homodimers including one of more of CD3-gamma chain, CD3-delta chain, CD3epsilon chain, and CD3-zeta chain polypeptide having a canonical human sequence and natural variants thereof that maintain the function of the canonical sequence; and any signaling complex including one or more of the foregoing CD3 homodimers or heterodimers. In some embodiments, a human CD3 protein biomarker-specific agent encompasses any biomarker-specific agent that specifically binds a structure (such as an epitope) within CD3-gamma chain polypeptide (such as the polypeptide at SEQ ID NO: 1), CD3-delta chain polypeptide (such as the polypeptide at SEQ ID NO: 2), CD3epsilon chain polypeptide (such as the polypeptide at SEQ ID NO: 3), or CD3-zeta chain polypeptide (such as the polypeptide at SEQ ID NO: 4), or that binds to a structure (such as an epitope) located within εγ-homodimer, εδ-heterodimer, or ζζ-homodimer.

CD8: CD8 is a heterodimeric, disulphide linked, transmembrane glycoprotein found on the cytotoxic-suppressor T cell subset, on thymocytes, on certain natural killer cells, and in a subpopulation of bone marrow cells. Exemplary sequences for (and isoforms and variants of) the human alpha- and beta-chain of the CD8 receptor can be found at Uniprot Accession Nos. P01732 (the canonical amino acid sequence for which is disclosed herein at SEQ ID NO: 5) and P10966 (the canonical amino acid sequence for which is disclosed herein at SEQ ID NO: 6), respectively. As used herein, the term "human CD8 protein biomarker" encompasses any CD8-alpha chain polypeptide having a canonical human sequence and natural variants thereof that maintain the function of the canonical sequence; any CD8-beta chain polypeptide having a canonical human sequence and natural variants thereof that maintain the function of the canonical sequence; any dimers including a CD8-alpha chain polypeptide having a canonical human sequence and natural variants thereof that maintain the function of the canonical sequence and/or a CD8-beta chain polypeptide having a canonical human sequence and natural variants thereof that maintain the function of the canonical sequence. In some embodiments, a human CD8 protein biomarker-specific agent encompasses any biomarker-specific agent that specifically binds a structure (such as an epitope) within CD8-alpha chain polypeptide (such as the polypeptide at SEQ ID NO: 6), CD8-beta chain polypeptide (such as the polypeptide at SEQ ID NO: 7), or that binds to a structure (such as an epitope) located within a CD8 dimer.

CTLA-4: CTLA-4 (also known as CD152), is an immune checkpoint protein expressed by the CTLA4 gene on chromosome 2 of humans. Exemplary sequences for (and isoforms and variants of) the human CTLA-4 protein can be found at Uniprot Accession No. P16410 (the canonical amino acid sequence for which is disclosed herein at SEQ ID NO: 7).

FoxP3: Forkhead box protein P3 (FoxP3) is a transcriptional regulator that is involved in the development and inhibitory function of regulatory T-cells ($T_{reg}$) that is encoded by the FOXP3 gene of the X chromosome. Exemplary sequences for (and isoforms and variants of) the human FOXP3 protein can be found at Uniprot Accession No. Q9BZS1 (the canonical amino acid sequence for which is disclosed herein at SEQ ID NO: 8). In some embodiments, a human FoxP3 protein biomarker-specific agent encompasses any biomarker-specific agent that specifically binds a structure (such as an epitope) within a human FoxP3 polypeptide (such as the polypeptide at SEQ ID NO: 8).

PD-1: Programmed death-1 (PD-1) is a member of the CD28 family of receptors encoded by the PDCD1 gene on chromosome 2. Exemplary sequences for (and isoforms and variants of) the human PD-1 protein can be found at Uniprot Accession No. Q15116 (the canonical amino acid sequence for which is disclosed herein at SEQ ID NO: 9). In some embodiments, a human PD-1 protein biomarker-specific agent encompasses any biomarker-specific agent that specifically binds a structure (such as an epitope) within a human PD-1 polypeptide (such as the polypeptide at SEQ ID NO: 9).

PD-L1: Programmed death ligand 1 (PD-L1) is a type 1 transmembrane protein encoded by the CD274 gene on chromosome 9. PD-L1 acts as a ligand for PD-1 and CD80. Exemplary sequences for (and isoforms and variants of) the human PD-L1 protein can be found at Uniprot Accession No. Q9NZQ7 (the canonical amino acid sequence for which is disclosed herein at SEQ ID NO: 10). In some embodiments, a human PD-L1 protein biomarker-specific agent encompasses any biomarker-specific agent that specifically binds a structure (such as an epitope) within a human PD-L1 polypeptide (such as the polypeptide at SEQ ID NO: 10).

PD-L2: Programmed death ligand 2 (PD-L2) is a transmembrane protein encoded by the PDCD1LG2 gene on chromosome 9. PD-L2 acts as a ligand for PD-1. Exemplary sequences for (and isoforms and variants of) the human PD-L2 protein can be found at Uniprot Accession No. Q9BQ51 (the canonical amino acid sequence for which is disclosed herein at SEQ ID NO: 11). In some embodiments, a human PD-L2 protein biomarker-specific agent encompasses any biomarker-specific agent that specifically binds a structure (such as an epitope) within a human PD-L2 polypeptide (such as the polypeptide at SEQ ID NO: 11).

TIM-3: T-cell immunoglobulin mucin receptor 3, also known as TIM-3, is an immune checkpoint protein encoded by the HAVCR2 gene located on human chromosome 5. Exemplary sequences for (and isoforms and variants of) the human TIM-3 protein can be found at Uniprot Accession No. Q8TDQ0 (the canonical amino acid sequence for which is disclosed herein at SEQ ID NO: 12). In some embodiments, a human TIM-3 protein biomarker-specific agent encompasses any biomarker-specific agent that specifically binds a structure (such as an epitope) within a human TIM3 polypeptide (such as the polypeptide at SEQ ID NO: 12).

LAG3: Lymphocyte activation gene 3 protein (LAG3) is a member of the immunoglobulin (Ig) superfamily encoded by the LAG3 gene on human chromosome 12. Exemplary sequences for (and isoforms and variants of) the human LAG3 protein can be found at Uniprot Accession No. P18627 (the canonical amino acid sequence for which is disclosed herein at SEQ ID NO: 13). In some embodiments, a human LAG3 protein biomarker-specific agent encompasses any biomarker-specific agent that specifically binds a structure (such as an epitope) within a human LAG3 polypeptide (such as the polypeptide at SEQ ID NO: 13).

IDO: Indoleamine 2,3-dioxygenase 1 (IDO) is an enzyme encoded by the IDO1 gene on human chromosome 8. Exemplary sequences for (and isoforms and variants of) the human IDO protein can be found at Uniprot Accession No. P14902 (the canonical amino acid sequence for which is disclosed herein at SEQ ID NO: 14). In some embodiments, a human IDO protein biomarker-specific agent encompasses any biomarker-specific agent that specifically binds a structure (such as an epitope) within a human IDO polypeptide (such as the polypeptide at SEQ ID NO: 14).

III. Generation of the Scoring Function

The scoring functions of the present methods and systems are derived from tumor samples from a cohort of patients with known outcomes having stage III colorectal cancer. A panel of biomarkers to test is selected, the samples of the cohort are stained for the biomarkers, and feature metrics for the biomarkers are calculated from one or more ROIs (which feature metrics optionally may be normalized and/or subject to upper or lower limits). The feature metrics for the samples are modeled against the outcomes using a one or more of a variety of models, including "time-to-event" models (such as Cox proportional hazard models for overall survival, disease-free survival, or progression-free survival) and binary event models (such as logistic regression models). Once a candidate continuous scoring function is identified, one or more cutoffs optionally may be selected to separate the cohort into groups according to their ICS (for example "high risk" and "low risk" groups), for example by using ROC curves, and the cutoffs are tested using Kaplan-Meier curves comparing the groups. The candidate continuous scoring function and cutoff combination showing the desired separation between groups is then selected. This function may then be used in an immune scoring system and methods as described herein.

The present scoring functions are based on a density of CD3+ cells located within an invasive margin (IM) region or a peri-tumoral (PT) region. Additional biomarkers may be included in the scoring function and/or CD3+ densities from different tissue compartments may also be included, so long as they do not significantly reduce the ability of the scoring function to prognose the subject or to predict the subject's response to a particular treatment course.

III.A. Samples and Sample Preparation for Generation of the Continuous Scoring Function The continuous scoring function is executed on a digital image of a tissue section obtained from a stage III colorectal tumor. The samples are typically tissue samples processed in a manner compatible with histochemical staining, including, for example, fixation (such as with a formalin-based fixative), embedding in a wax matrix (such as paraffin), and sectioning (such as with a microtome). No specific processing step is required by the present disclosure, so long as the sample obtained is compatible with histochemical staining of the sample for the biomarkers of interest and generating a digital image of the stained sample. In a specific embodiment, the sample is a microtome section of a formalin-fixed, paraffin-embedded (FFPE) tissue samples of a stage III colorectal cancer tumor.

III.B. Biomarker Panels

In an embodiment, at least one tissue section of the stage III colorectal sample is labeled with a human CD3 protein biomarker-specific reagent in combination with appropriate detection reagents, and a density of CD3+ cells is evaluated. Additionally, the tumor may be classified on the basis of mismatch repair and/or microsatellite stability status.

Mismatch repair status (also termed "MMR") typically involves evaluating the expression and/or methylation status of four genes involved in mismatch repair: hPMS2, hMLH1, hMSH2, and hMSH6. Canonical protein sequences are disclosed at SEQ ID NO: 15-18, respectively. A tumor having deficient expression of any one of these four is determined to have deficient mismatch repair (termed "dMMR"), while a tumor that is not deficient in expression of any of these genes is determined to have proficient MMR (termed "pMMR"). MMR status may be determined, for example, a protein-based assay (such as by immunoassay, such as a solid-phase enzyme immunoassay (e.g., ELISA) or immunohistochemical assay) or a polymerase chain reaction (PCR) assay (such as a real-time reverse transcriptase PCR assay).

Microsatellite instability ("MSI") is caused by MMR deficiency. As a result, alterations in the length of microsatellite loci begin to accumulate. Assays for evaluating MSI status are well known in the art. See, e.g., Murphy et al., J. Mol. Diagn., Vol. 8, Issue 3, pp. 305-11 (July 2006); Esemuede et al., Ann. Surg. Oncol., vol. 17, Issue 12, pp. 3370-78 (December 2010); Mukherjee et al., Hereditary Cancer in Clinical Practice, Vol. 8, Issue 9 (2010); MSI Analysis System (Promega) (evaluation of seven markers for MSI-high phenotype, including five nearly monomorphic mononucleotide repeat markers (BAT-25, BAT-26, MONO-27, NR-21 and NR-24) and two highly polymorphic pentanucleotide repeat markers (Penta C and Penta D)).

III.C. Histochemical Staining of Samples

The digital image on which the continuous scoring function is applied may be obtained from a histochemically-stained tissue section. Sections of the samples are stained by applying one or more biomarker-specific reagents in combination with a set of appropriate detection reagents to generate a biomarker-stained section. Biomarker staining is typically accomplished by contacting a section of the sample with a biomarker-specific reagent under conditions that facilitate specific binding between the biomarker and the biomarker-specific reagent. The sample is then contacted with a set of detection reagents that interact with the biomarker-specific reagent to facilitate deposition a detectable moiety in close proximity the biomarker, thereby generating a detectable signal localized to the biomarker. Typically, wash steps are performed between application of different reagents to prevent unwanted non-specific staining of tissues.

The biomarker-specific reagent facilitates detection of the biomarker by mediating deposition of a detectable moiety in close proximity to the biomarker-specific reagent.

In some embodiments, the detectable moiety is directly conjugated to the biomarker-specific reagent, and thus is deposited on the sample upon binding of the biomarker-specific reagent to its target (generally referred to as a direct labeling method). Direct labeling methods are often more directly quantifiable, but often suffer from a lack of sensitivity. In other embodiments, deposition of the detectable moiety is effected by the use of a detection reagent associated with the biomarker-specific reagent (generally referred to as an indirect labeling method). Indirect labeling methods have the increase the number of detectable moieties that can be deposited in proximity to the biomarker-specific reagent, and thus are often more sensitive than direct labeling methods, particularly when used in combination with dyes.

In some embodiments, an indirect method is used, wherein the detectable moiety is deposited via an enzymatic reaction localized to the biomarker-specific reagent. Suitable enzymes for such reactions are well-known and include, but are not limited to, oxidoreductases, hydrolases, and peroxidases. Specific enzymes explicitly included are horseradish peroxidase (HRP), alkaline phosphatase (AP), acid phosphatase, glucose oxidase, β-galactosidase, β-glucuronidase, and β-lactamase. The enzyme may be directly conjugated to the biomarker-specific reagent, or may be indirectly associated with the biomarker-specific reagent via a labeling conjugate. As used herein, a "labeling conjugate" comprises:

(a) a specific detection reagent; and
(b) an enzyme conjugated to the specific detection reagent, wherein the enzyme is reactive with the chromogenic substrate, signaling conjugate, or enzyme-reactive dye under appropriate reaction conditions to effect in situ generation of the dye and/or deposition of the dye on the tissue sample.

In non-limiting examples, the specific detection reagent of the labeling conjugate may be a secondary detection reagent (such as a species-specific secondary antibody bound to a primary antibody, an anti-hapten antibody bound to a hapten-conjugated primary antibody, or a biotin-binding protein bound to a biotinylated primary antibody), a tertiary detection reagent (such as a species-specific tertiary antibody bound to a secondary antibody, an anti-hapten antibody bound to a hapten-conjugated secondary antibody, or a biotin-binding protein bound to a biotinylated secondary antibody), or other such arrangements. An enzyme thus localized to the sample-bound biomarker-specific reagent can then be used in a number of schemes to deposit a detectable moiety.

In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxido-reductase enzyme (such as horseradish peroxidase) along with a water soluble metal ion, an oxidizing agent and a reducing agent, again to for form a detectable precipitate.

(See, for example, U.S. Pat. No. 6,670,113, which is incorporated by reference herein in its entirety).

In some embodiments, the enzymatic action occurs between the enzyme and the dye itself, wherein the reaction converts the dye from a non-binding species to a species deposited on the sample. For example, reaction of DAB with a peroxidase (such as horseradish peroxidase) oxidizes the DAB, causing it to precipitate.

In yet other embodiments, the detectable moiety is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the latent reactive moiety is directly conjugated to a dye, such as N,N'-biscarboxypentyl-5,5'-disulfonato-indo-dicarbocyanine (Cy5), 4-(dimethylamino) azobenzene-4'-sulfonamide (DABSYL), tetramethylrhodamine (DISCO Purple), and Rhodamine 110 (Rhodamine). In other examples, the latent reactive moiety is conjugated to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB); and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

Non-limiting examples of biomarker-specific reagent and detection reagent combinations are set forth in Table 1 are specifically included.

TABLE 1

| A. Biomarker-specific reagent linked directly to detectable moiety | |
|---|---|
| Biomarker-specific reagent-Dye conjugate | |
| B. Biomarker-specific reagent linked to enzyme reacting with detectable moiety | |
| Biomarker-specific reagent-Enzyme conjugate + DAB | |
| Biomarker-specific reagent-Enzyme conjugate + Chromogen | |
| C. Biomarker-specific reagent linked to Enzyme reacting with signaling conjugate | |
| C1. Signaling conjugate comprises detectable moiety | Biomarker-specific reagent-Enzyme conjugate + QM-Dye conjugate |
| | Biomarker-specific reagent-Enzyme conjugate + Tyramide-Dye conjugate |
| C2. Signaling conjugate comprises enzyme that reacts directly with detectable moiety | Biomarker-specific reagent-Enzyme conjugate + QM-Enzyme conjugate + DAB |
| | Biomarker-specific reagent-Enzyme conjugate + QM-Enzyme conjugate + Chromogen |
| | Biomarker-specific reagent-Enzyme conjugate + Tyramide-Enzyme conjugate + DAB |
| | Biomarker-specific reagent-Enzyme conjugate + Tyramide-Enzyme conjugate + Chromogen |
| C3. Signaling conjugate comprises enzyme that reacts with second signaling conjugate comprising detectable moiety | Biomarker-specific reagent-Enzyme conjugate + QM-Enzyme conjugate + QM-Dye conjugate |
| | Biomarker-specific reagent-Enzyme conjugate + QM-Enzyme conjugate + Tyramide-Dye conjugate |
| | Biomarker-specific reagent-Enzyme conjugate + Tyramide-Enzyme conjugate + QM-Dye conjugate |
| | Biomarker-specific reagent-Enzyme conjugate + Tyramide-Enzyme conjugate + Tyramide-Dye conjugate |
| C4. Signaling conjugate comprises member of a specific binding pair and other member of binding pair is linked to detectable moiety | Biomarker-specific reagent-Enzyme conjugate + Tyramide-(biotin/hapten) conjugate + Dye-(avidin/anti-hapten biomarker-specific reagent) conjugate |
| | Biomarker-specific reagent-Enzyme conjugate + QM-(biotin/hapten) conjugate + Dye-(avidin/anti-hapten biomarker-specific reagent) conjugate |
| C5. Signaling conjugate comprises member of a specific binding pair and other member of binding pair is linked to enzyme reactive with detectable moiety | Biomarker-specific reagent-Enzyme conjugate + QM-(biotin/hapten) conjugate + Enzyme-(avidin/anti-hapten biomarker-specific reagent) conjugate + DAB |
| | Biomarker-specific reagent-Enzyme conjugate + QM-(biotin/hapten) conjugate + Enzyme-(avidin/anti-hapten biomarker-specific reagent) conjugate + Chromogen |
| | Biomarker-specific reagent-Enzyme conjugate + Tyramide-(biotin/hapten) conjugate + Enzyme-(avidin/anti-hapten biomarker-specific reagent) conjugate + DAB |

TABLE 1-continued

| | |
|---|---|
| | Biomarker-specific reagent-Enzyme conjugate + Tyramide-(biotin/hapten) conjugate + Enzyme-(avidin/anti-hapten biomarker-specific reagent) conjugate + Chromogen |
| C6. Signaling conjugate comprises member of a specific binding pair and other member of binding pair is linked to enzyme reactive with second detectable moiety linked to a detectable moiety | Biomarker-specific reagent-Enzyme conjugate + QM-(biotin/hapten) conjugate + Enzyme-(avidin/anti-hapten biomarker-specific reagent) conjugate + Tyramide-Dye conjugate |
| | Biomarker-specific reagent-Enzyme conjugate + QM-(biotin/hapten) conjugate + Enzyme-(avidin/anti-hapten biomarker-specific reagent) conjugate + QM-Dye conjugate |
| | Biomarker-specific reagent-Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent-Enzyme conjugate + Tyramide-(biotin/hapten) conjugate + Enzyme-(avidin/anti-hapten biomarker-specific reagent) conjugate + QM-Dye conjugate |
| D. Biomarker-specific reagent linked to member of specific binding pair | |
| D1. Dye linked to other member of specific binding pair | Biomarker-specific reagent-(biotin/hapten) conjugate + Dye-(avidin/anti-hapten biomarker-specific reagent) conjugate |
| D2. Enzyme linked to other member of specific binding pair, wherein the enzyme is reactive with detectable moiety | Biomarker-specific reagent-(biotin/hapten) conjugate + Enzyme-(avidin/anti-hapten biomarker-specific reagent) conjugate + DAB |
| | Biomarker-specific reagent-(biotin/hapten) conjugate + Enzyme-(avidin/anti-hapten biomarker-specific reagent) conjugate + Chromogen |
| | Biomarker-specific reagent-(biotin/hapten) conjugate + Enzyme-(avidin/anti-hapten biomarker-specific reagent) conjugate + QM-Dye conjugate |
| | Biomarker-specific reagent-(biotin/hapten) conjugate + Enzyme-(avidin/anti-hapten biomarker-specific reagent) conjugate + Tyramide-Dye conjugate |
| E. Secondary detection reagent linked directly to detectable moiety | |
| Biomarker-specific reagent + 2° specific detection reagent-Dye conjugate | |
| F. Secondary detection reagent linked to Enzyme reacting with detectable moiety | |
| Biomarker-specific reagent + 2° specific detection reagent-Enzyme conjugate + DAB | |
| Biomarker-specific reagent + 2° specific detection reagent-Enzyme conjugate + Chromogen | |
| G. Secondary detection reagent linked to Enzyme reacting with signaling conjugate | |
| G1. Signaling conjugate comprises detectable moiety | Biomarker-specific reagent + 2° specific detection reagent-Enzyme conjugate + QM-Dye conjugate |
| | Biomarker-specific reagent + 2° specific detection reagent-Enzyme conjugate + Tyramide-Dye conjugate |
| G2. Signaling conjugate comprises enzyme that reacts directly with detectable moiety | Biomarker-specific reagent + 2° specific detection reagent-Enzyme conjugate + QM-Enzyme conjugate + DAB |
| | Biomarker-specific reagent + 2° specific detection reagent-Enzyme conjugate + QM-Enzyme conjugate + Chromogen |
| | Biomarker-specific reagent + 2° specific detection reagent-Enzyme conjugate + Tyramide-Enzyme conjugate + DAB |
| | Biomarker-specific reagent + 2° specific detection reagent-Enzyme conjugate + Tyramide-Enzyme conjugate + Chromogen |
| G3. Signaling conjugate comprises enzyme that reacts with second signaling conjugate comprising detectable moiety | Biomarker-specific reagent + 2° specific detection reagent-Enzyme conjugate + QM-Enzyme conjugate + QM-Dye conjugate |
| | Biomarker-specific reagent + 2° specific detection reagent-Enzyme conjugate + QM-Enzyme conjugate + Tyramide-Dye conjugate |
| | Biomarker-specific reagent + 2° specific detection reagent-Enzyme conjugate + Tyramide-Enzyme conjugate + QM-Dye conjugate |
| | Biomarker-specific reagent + 2° specific detection reagent-Enzyme conjugate + Tyramide-Enzyme conjugate + Tyramide-Dye conjugate |

TABLE 1-continued

| | |
|---|---|
| G4. Signaling conjugate comprises member of a specific binding pair and other member of binding pair is linked to detectable moiety | Biomarker-specific reagent + 2° specific detection reagent-Enzyme conjugate + Tyramide-(biotin/hapten) conjugate + Dye-(avidin/anti-hapten biomarker-specific reagent) conjugate<br>Biomarker-specific reagent + 2° specific detection reagent-Enzyme conjugate + QM-(biotin/hapten) conjugate + Dye-(avidin/anti-hapten biomarker-specific reagent) conjugate |
| G5. Signaling conjugate comprises member of a specific binding pair and other member of binding pair is linked to enzyme reactive with detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + DAB<br>Biomarker-specific reagent + 2° specific detection reagent-Enzyme conjugate + QM-(biotin/hapten) conjugate + Enzyme-(avidin/anti-hapten biomarker-specific reagent) conjugate + Chromogen<br>Biomarker-specific reagent + 2° specific detection reagent-Enzyme conjugate + Tyramide-(biotin/hapten) conjugate + Enzyme-(avidin/anti-hapten biomarker-specific reagent) conjugate + DAB<br>Biomarker-specific reagent + 2° specific detection reagent-Enzyme conjugate + Tyramide-(biotin/hapten) conjugate + Enzyme-(avidin/anti-hapten biomarker-specific reagent) conjugate + Chromogen |
| G6. Signaling conjugate comprises member of a specific binding pair and other member of binding pair is linked to enzyme reactive with second detectable moiety linked to a detectable moiety | Biomarker-specific reagent + 2° specific detection reagent-Enzyme conjugate + QM-(biotin/hapten) conjugate + Enzyme-(avidin/anti-hapten biomarker-specific reagent) conjugate + Tyramide-Dye conjugate<br>Biomarker-specific reagent + 2° specific detection reagent-Enzyme conjugate + QM-(biotin/hapten) conjugate + Enzyme-(avidin/anti-hapten biomarker-specific reagent) conjugate + QM-Dye conjugate<br>Biomarker-specific reagent + 2° specific detection reagent-Enzyme conjugate + Tyramide-(biotin/hapten) conjugate + Enzyme-(avidin/anti-hapten biomarker-specific reagent) conjugate + Tyramide-Dye conjugate<br>Biomarker-specific reagent + 2° specific detection reagent-Enzyme conjugate + Tyramide-(biotin/hapten) conjugate + Enzyme-(avidin/anti-hapten biomarker-specific reagent) conjugate + QM-Dye conjugate |
| H. Secondary detection reagent linked to member of specific binding pair | |
| H1. Dye linked to other member of specific binding pair | Biomarker-specific reagent + 2° specific detection reagent-(biotin/hapten) conjugate + Dye-(avidin/anti-hapten biomarker-specific reagent) conjugate |
| H2. Enzyme linked to other member of specific binding pair, wherein the enzyme is reactive with detectable moiety | Biomarker-specific reagent + 2° specific detection reagent-(biotin/hapten) conjugate + Enzyme-(avidin/anti-hapten biomarker-specific reagent) conjugate + DAB<br>Biomarker-specific reagent + 2° specific detection reagent-(biotin/hapten) conjugate + Enzyme-(avidin/anti-hapten biomarker-specific reagent) conjugate + Chromogen<br>Biomarker-specific reagent + 2° specific detection reagent-(biotin/hapten) conjugate + Enzyme-(avidin/anti-hapten biomarker-specific reagent) conjugate + QM-Dye conjugate<br>Biomarker-specific reagent + 2° specific detection reagent-(biotin/hapten) conjugate + Enzyme-(avidin/anti-hapten biomarker-specific reagent) conjugate + Tyramide-Dye conjugate |
| I. Tertiary specific detection reagent linked directly to detectable moiety | |

Biomarker-specific reagent + 2° specific detection reagent + 3° specific detection reagent-Dye conjugate J. Tertiary specific detection reagent linked to Enzyme reacting with detectable moiety Biomarker-specific reagent + 2° specific detection reagent + 3° specific detection reagent-Enzyme conjugate + DAB
Biomarker-specific reagent + 2° specific detection reagent + 3° specific detection reagent-Enzyme conjugate + Chromogen K. Tertiary specific detection reagent linked to Enzyme reacting with signaling conjugate

| | |
|---|---|
| K1. Signaling conjugate comprises detectable moiety | Biomarker-specific reagent + 2° specific detection reagent + 3° specific detection reagent-Enzyme conjugate + QM-Dye conjugate<br>Biomarker-specific reagent + 2° specific detection reagent + 3° specific detection reagent-Enzyme conjugate + Tyramide-Dye conjugate |

TABLE 1-continued

| | |
|---|---|
| K2. Signaling conjugate comprises enzyme that reacts directly with detectable moiety | Biomarker-specific reagent + 2° specific detection reagent + 3° specific detection reagent-Enzyme conjugate + QM-Enzyme conjugate + DAB<br>Biomarker-specific reagent + 2° specific detection reagent + 3° specific detection reagent-Enzyme conjugate + QM-Enzyme conjugate + Chromogen<br>Biomarker-specific reagent + 2° specific detection reagent + 3° specific detection reagent-Enzyme conjugate + Tyramide-Enzyme conjugate + DAB<br>Biomarker-specific reagent + 2° specific detection reagent + 3° specific detection reagent-Enzyme conjugate + Tyramide-Enzyme conjugate + Chromogen |
| K3. Signaling conjugate comprises enzyme that reacts with second signaling conjugate comprising detectable moiety | Biomarker-specific reagent + 2° specific detection reagent + 3° specific detection reagent-Enzyme conjugate + QM-Enzyme conjugate + QM-Dye conjugate<br>Biomarker-specific reagent + 2° specific detection reagent + 3° specific detection reagent-Enzyme conjugate + QM-Enzyme conjugate + Tyramide-Dye conjugate<br>Biomarker-specific reagent + 2° specific detection reagent + 3° specific detection reagent-Enzyme conjugate + Tyramide-Enzyme conjugate + QM-Dye conjugate<br>Biomarker-specific reagent + 2° specific detection reagent + 3° specific detection reagent-Enzyme conjugate + Tyramide-Enzyme conjugate + Tyramide-Dye conjugate |
| K4. Signaling conjugate comprises member of a specific binding pair and other member of binding pair is linked to detectable moiety | Biomarker-specific reagent + 2° specific detection reagent + 3° specific detection reagent-Enzyme conjugate + Tyramide-(biotin/hapten) conjugate + Dye-(avidin/anti-hapten biomarker-specific reagent) conjugate<br>Biomarker-specific reagent + 2° specific detection reagent + 3° specific detection reagent-Enzyme conjugate + QM-(biotin/hapten) conjugate + Dye-(avidin/anti-hapten biomarker-specific reagent) conjugate |
| K5. Signaling conjugate comprises member of a specific binding pair and other member of binding pair is linked to enzyme reactive with detectable moiety | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + DAB<br>Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Chromogen<br>Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + DAB<br>Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + Chromogen |
| K6. Signaling conjugate comprises member of a specific binding pair and other member of binding pair is linked to enzyme reactive with second detectable moiety linked to a detectable moiety | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Tyramide-Dye conjugate<br>Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + QM-Dye conjugate<br>Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + Tyramide-Dye conjugate<br>Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + QM-Dye conjugate |
| L. Tertiary specific detection reagent linked to member of specific binding pair | |
| L1. Dye linked to other member of specific binding pair | Biomarker-specific reagent + 2° specific detection reagent + 3° specific detection reagent-(biotin/hapten) conjugate + Dye-(avidin/anti-hapten biomarker-specific reagent) conjugate |

TABLE 1-continued

| | |
|---|---|
| L2. Enzyme linked to other member of specific binding pair, wherein the enzyme is reactive with detectable moiety | Biomarker-specific reagent + 2° specific detection reagent + 3° specific detection reagent-(biotin/hapten) conjugate + Enzyme-(avidin/anti-hapten biomarker-specific reagent) conjugate + DAB |
| | Biomarker-specific reagent + 2° specific detection reagent + 3° specific detection reagent-(biotin/hapten) conjugate + Enzyme-(avidin/anti-hapten biomarker-specific reagent) conjugate + Chromogen |
| | Biomarker-specific reagent + 2° specific detection reagent + 3° specific detection reagent-(biotin/hapten) conjugate + Enzyme-(avidin/anti-hapten biomarker-specific reagent) conjugate + QM-Dye conjugate |
| | Biomarker-specific reagent + 2° specific detection reagent + 3° specific detection reagent-(biotin/hapten) conjugate + Enzyme-(avidin/anti-hapten biomarker-specific reagent) conjugate + Tyramide-Dye conjugate |

In a specific embodiment, the biomarker-specific reagents and the specific detection reagents set forth in Table 1 are antibodies. As would be appreciated by a person having ordinary skill in the art, the detection scheme for each of the biomarker-specific reagent may be the same, or it may be different.

Non-limiting examples of commercially available detection reagents or kits comprising detection reagents suitable for use with present methods include: VENTANA ultraView detection systems (secondary antibodies conjugated to enzymes, including HRP and AP); VENTANA iVIEW detection systems (biotinylated anti-species secondary antibodies and streptavidin-conjugated enzymes); VENTANA OptiView detection systems (OptiView) (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); VENTANA OptiView Amplification system (Anti-species secondary antibody conjugated to a hapten, an anti-hapten tertiary antibody conjugated to an enzyme multimer, and a tyramide conjugated to the same hapten. In use, the secondary antibody is contacted with the sample to effect binding to the primary antibody. Then the sample is incubated with the anti-hapten antibody to effect association of the enzyme to the secondary antibody. The sample is then incubated with the tyramide to effect deposition of additional hapten molecules. The sample is then incubated again with the anti-hapten antibody to effect deposition of additional enzyme molecules. The sample is then incubated with the detectable moiety to effect dye deposition); VENTANA DISCOVERY, DISCOVERY OmniMap, DISCOVERY UltraMap anti-hapten antibody, secondary antibody, chromogen, fluorophore, and dye kits, each of which are available from Ventana Medical Systems, Inc. (Tucson, Arizona); PowerVision and PowerVision+ IHC Detection Systems (secondary antibodies directly polymerized with HRP or AP into compact polymers bearing a high ratio of enzymes to antibodies); and DAKO EnVision™+ System (enzyme labeled polymer that is conjugated to secondary antibodies).

III.D Counterstaining

If desired, the biomarker-stained slides may be counterstained to assist in identifying morphologically relevant areas for identifying ROIs, either manually or automatically. Examples of counterstains include chromogenic nuclear counterstains, such as hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear chromogenic stains, such as eosin (stains pink); fluorescent nuclear stains, including 4', 6-diamino-2-pheylindole (DAPI, stains blue), propidium iodide (stains red), Hoechst stain (stains blue), nuclear green DCS1 (stains green), nuclear yellow (Hoechst S769121, stains yellow under neutral pH and stains blue under acidic pH), DRAQ5 (stains red), DRAQ7 (stains red); fluorescent non-nuclear stains, such as fluorophore-labelled phalloidin, (stains filamentous actin, color depends on conjugated fluorophore).

III.E. Morphological Staining of Samples

In certain embodiments, it may also be desirable to morphologically stain a serial section of the biomarker-stained section. This section can be used to identify the ROIs from which scoring is conducted. Basic morpohological staining techniques often rely on staining nuclear structures with a first dye, and staining cytoplasmic structures with a second stain. Many morphological stains are known, including but not limited to, hematoxylin and eosin (H&E) stain and Lee's Stain (Methylene Blue and Basic Fuchsin). In a specific embodiment, at least one serial section of each biomarker-stained slide is H&E stained. Any method of applying H&E stain may be used, including manual and automated methods. In an embodiment, at least one section of the sample is an H&E stained sampled stained on a automated staining system. Automated systems for performing H&E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH.

III.F. ROI Selection and Feature Metric Calculation

In an embodiment, the continuous scoring function is applied to a feature vector derived from the digital image, wherein the feature vector includes a density of CD3+ cells in an invasive margin (IM) region or a peri-tumoral (PT) region of the tumor section.

In some embodiments, the ROI may be manually identified by a trained reader, who delineates area(s) corresponding to an IM or PT region, which delineated regions may then be used as the ROI for calculation of the CD3+ cell density. In other embodiments, a computer-implemented system may assist the user in annotating the ROI (termed, "semi-automated ROI annotation"). For example, the user may mark a whole tumor region in the digital image. The computer-implemented system may then automatically define a region extending a pre-defined distance (for example, 0.5 mm, 1 mm, or 1.5 mm) beyond the edge of the tumor region delineated by the trained user, which is used as the IM. In other embodiments, the computer-implemented system may automatically define a region that extends a pre-defined distance beyond the edge of the tumor region (for example, 0.5 mm, 1 mm, or 1.5 mm) and a pre-defined distance (for example, 0.5 mm, 1.0 mm, or 1.5 mm) inside of the tumor region delineated by the trained user, which is then used as the ROI (in this case referred to as a peritumoral (PT) ROI). In each embodiment set forth in this paragraph, the ROI may be identified directly in a biomarker-stained section, or may be identified in a serial section of the biomarker-stained section and then registered to the digital image of the biomarker-stained slide.

The feature metric is calculated by applying a metric of the ROI to the CD3+ expression data within the ROI. Examples of ROI metrics that could be used for feature metric calculation include, for example, area of the ROI or length of an edge defining the ROI (such as length of an edge of a whole tumor region around which the IM region is defined). Specific examples of feature metrics include:
(a) an area density of CD3+ cells within the ROI (number of positive cells over area of ROI), and
(b) a linear density of Cd3+ cells (total number of cells expressing the biomarker within the ROI over the linear length of an edge defining the ROI, such as a line denoting a tumor region around which the IM region is calculated), The feature metric may be based directly on the raw counts in the ROI (referred to hereafter as a "Total metric"), or based on a mean or median feature metric of a plurality of control regions within the ROI (hereafter referred to as a "global metric"). These two approaches are illustrated at FIG. 1. In both cases, an image of an IHC slide is provided having an ROI annotated (denoted as the region within the dashed line) and objects of interest identified (e.g., CD3+ cells). For the total metric approach, the feature metric is calculated by quantitating the relevant metric of all the marked features within the ROI ("ROI object metric") and dividing the ROI object metric (such as total marked objects or total area of marked biomarker expression, etc.) by the ROI metric (such as the area of the ROI, number of total cells within ROI, etc.) (step A1). For the global metric approach, a plurality of control regions (illustrated by the open circles) is overlaid on the ROI (step B1). A control region metric ("CR metric") is calculated by quantitating the relevant metric of the control region ("CR Object Metric") (such as total marked objects within the control region or total area of marked biomarker expression within the control region, etc.) and dividing it by a control region ROI metric ("CR ROI Metric") (such as the area of the control region, number of total cells within the control region, etc.) (step B2). A separate CR metric is calculated for each control region. The global metric is obtained by calculating the mean or the median of all CR metrics (Step B3).

Where control regions are used, any method of overlaying control regions for metric processing may be used. In a specific embodiment, the ROI may be divided into a plurality of grid spaces (which may be equal sized, randomly sized, or some combination of varying sizes), each grid space constituting a control region. Alternatively, a plurality of control regions having known sizes (which may be the same or different) may be placed adjacent to each other or overlapping one another to cover substantially the entire ROI. Other methods and arrangements may also be used, so long as the output is a feature metric for the ROI that can be compared across different samples.

If desired, the calculated feature metrics may optionally converted to a normalized feature vector.

In the typical example, before the continuous scoring function is modeled, the feature metrics calculated for the samples of the cohort are plotted, and the distribution is evaluated to identify any rightward or leftward skew. Biologically meaningful cutoffs (maximum cutoffs for right-skewed distributions, and/or minimum cutoffs for left-skewed distributions) are identified, and each sample having a value beyond the cutoff (above in the case of a right-skewed distribution, or below in the case of left-skewed distribution) is assigned a feature metric equal to the cutoff value. The cutoff value (hereafter referred to as the "normalization factor") is then applied to each feature metric. In the case of a right-skewed distribution, the feature metric is divided by the normalization factor to obtain the normalized feature metric, in which case the feature metric is expressed on a maximum scale (i.e. the value of the normalized metric will not exceed a pre-determined maximum, such as 1, 10, 100, etc.). Similarly, in the case of a left-skewed distribution, the feature metric is divided by the normalization factor to obtain the normalized feature metric, in which case the feature metric is expressed on a minimum scale (i.e. the value of the normalized metric will not fall below a pre-determined minimum, such as 1, 10, 100, etc.). If desired, the normalized feature metric may also be multiplied by or divided by a pre-determined constant value to obtain the desired scale (for example, for right skewed distributions, multiplied by 100 to obtain a percentage of the normalization factor instead of a fraction of the normalization factor). Normalized feature metrics may be calculated for test samples by applying the normalization factor and/or maximum and/or minimum cutoffs identified for modeling to the feature metric calculated for the test sample.

III.F. Modeling the Continuous Scoring Function

In order to generate the continuous scoring function, the feature metrics from a cohort of patients are modeled for their ability to predict the relative tumor prognosis, risk of progression, and/or likelihood of responding to a particular treatment course. In an embodiment, a "time-to-event" model is used. These models test each variable for the ability to predict the relative risk of a defined event occurring at any given time point. The "event" in such a case is typically overall survival, disease-free survival, and progression-free survival. In one example, the "time-to event" model is a Cox proportional hazard model for overall survival, disease-free survival, or progression-free survival. The Cox proportional hazard model can be written as formula 1:

$$=\exp(b_1 X_1 + b_2 X_2 + \ldots b_p X_p) \quad \text{Formula 1}$$

in each case, wherein $X_1, X_2, \ldots X_p$ are the values of the feature metric(s) (which optionally may be subject to maximum and/or minimum cutoffs, and/or normalization), $b_1, b_2 \ldots b_p$ are constants extrapolated from the model for each of the feature metric(s). For each patient sample of the test cohort, data is obtained regarding the outcome being tracked (time to death, time to recurrence, or time to progression)

and the feature metric for each biomarker being analyzed. Candidate Cox proportional models are generated by entering the feature metric data and survival data for each individual of the cohort into a computerized statistical analysis software suite (such as The R Project for Statistical Computing (available at https://www.r-project.org/), SAS, MATLAB, among others). Each candidate model is tested for predictive ability using a concordance index, such as C-index. The model having the highest concordance score using the selected concordance index is selected as the continuous scoring function.

Additionally, one or more stratification cutoffs may be selected to separate the patients into "risk bins" according to relative risk (such as "high risk" and "low risk," quartiles, deciles, etc.). In one example, stratification cutoffs are selected using receiver operator characteristic (ROC) curves. ROC curves allow users to balance the sensitivity of the model (i.e. prioritize capturing as many "positive" or "high risk" candidates as possible) with the specificity of the model (i.e. minimizing false-positives for "high risk candidates"). In an embodiment, a cutoff between high risk and low risk bins for overall survival, disease-free survival or progression-free survival is selected, the cutoff chosen having the sensitivity and specificity balanced.

IV. Immune Context Scoring with a Continuous Scoring Function

After the continuous scoring function has been modeled and optional stratification cutoffs have been selected, the continuous scoring function may be applied to images of test samples to calculate an immune context score (ICS) for the test sample. The test samples are typically similar to the sample types used for modeling the continuous scoring function, except that outcomes are not yet known. The test samples are stained for the biomarkers relevant to the continuous scoring function (e.g., human CD3 protein) and the relevant feature metrics are calculated, and if they are being used, the normalization factor(s) and/or maximum and/or minimum cutoffs are applied to the feature metrics to obtain the normalized feature metrics. The ICS is calculated by applying the continuous scoring function to the feature metrics or the normalized feature metrics. The immune context score may then be integrated into diagnostic and/or treatment decisions by a clinician.

Thus, in an embodiment, the immune context score may be applied in a method for selecting a treatment for a subject having a stage III colorectal cancer, said method comprising:
   (a) obtaining said immune context score (ICS) for the colorectal tumor of the subject as described elsewhere herein and, in particular, from annotating an invasive margin (IM) or a peri-tumoral (PT) region of interest (ROI) on a digital image of a test sample of a stage III colorectal tumor;
   (b) optionally, obtaining a mismatch repair (MMR) status or microsatellite instability (MSI) status of the colorectal tumor; and
   (c) selecting a treatment for the subject based upon the ICS and optionally further based upon the mismatch repair status.

Typically, the aforementioned method shall be carried out ex vivo, i.e. based on a digital image of a test sample.

In yet an embodiment of the aforementioned method of the invention, selecting a treatment comprises:
   (c1) if the ICS is indicative of a poor prognosis, selecting a treatment comprising a full course of an adjuvant chemotherapy; and
   (c2) if the ICS is indicative of a good prognosis, selecting a treatment comprising a reduced course of an adjuvant chemotherapy or that does not comprise an adjuvant chemotherapy.

In yet an embodiment of the aforementioned method of the invention, selecting a treatment comprises:
   (c1) if the tumor has a dMMR or $MST^{high}$ status and the ICS is indicative of a good prognosis, selecting a treatment comprising a checkpoint inhibitor-directed therapy and optionally further comprising an adjuvant chemotherapy; and
   (c2) if the tumor has a dMMR or $MST^{high}$ status and the ICS is indicative of a poor prognosis, selecting a treatment comprising an adjuvant chemotherapy and optionally further comprising a checkpoint inhibitor-directed therapy;
   (c3) if the tumor has a pMMR or $MSI^{low}$ status and the ICS is indicative of a good prognosis, selecting a treatment comprising an adjuvant chemotherapy and optionally further comprising a checkpoint inhibitor-directed therapy; and
   (c4) if the tumor has a pMMR or $MSI^{low}$ status and the ICS is indicative of a poor prognosis, selecting a treatment comprising an adjuvant chemotherapy without a checkpoint inhibitor-directed therapy.

More typically, (c1) and (c3) comprise a reduced course of adjuvant chemotherapy or (c1) and (c3) do not comprise adjuvant chemotherapy.

More typically, (c2) and (c4) comprise a full course of adjuvant chemotherapy.

In some embodiments of the aforementioned method of the invention, the checkpoint inhibitor-directed therapy comprises a PD-1-directed therapy or a PD-L1-directed therapy.

In yet another embodiment of the aforementioned method, said method is carried out by using a computer or a computer network, e.g., as described elsewhere herein in more detail.

Moreover, in an embodiment, the invention also provides for the use of an immune context score obtainable by the aforementioned methods of the invention for selecting a treatment for a subject having a stage III colorectal cancer.

IV.A. Clinical Applications of Certain Immune Context Scores

Stage III colorectal cancers are cancers that have grown through the wall of the colon or rectum, and possibly into nearby tissue, and have spread to the lymph nodes, but have not yet spread to distant sites. The continuous scoring function is developed for stage III colorectal cancer as a function of patient prognosis (for example, using overall survival, disease-free survival or progression-free survival). In a specific embodiment, the continuous scoring function uses a CD3+ density in an ROI comprising an invasive margin (which density may be normalized and/or subject to maximum and/or minimum cutoffs). In an embodiment, the densities are area densities or linear densities. In an embodiment, each density is derived from a total metric or global metric. In an embodiment, the continuous scoring function is prognostic of 5 year disease-free survival. In another embodiment, the continuous scoring function is prognostic of 5 year progression-free survival. In another embodiment, the continuous scoring function is prognostic of 5 year overall survival.

In one specific embodiment, the continuous scoring function is used for selecting stage III colorectal cancer patients for receipt of a chemotherapy is developed, wherein the continuous scoring function incorporates CD3-positive area cell densities within an ROI comprising or consisting of an invasive margin (IM) area. Current treatment protocols typically include surgical removal of the tumor and nearby lymph nodes and chemotherapy. For colon cancers, chemotherapy is typically administered as an adjuvant treatment. In rectal cancer, chemotherapy is typically administered in combination with radiation therapy (termed chemoradiation) before surgical resection. In some rectal cases, chemotherapy may be administered alone first, followed by chemoradiation, followed by surgical resection. In yet other cases, stage III rectal cancer may be treated by surgical resection, followed by chemotherapy or chemoradiation. Common chemotherapies used in stage III colorectal cancer include FOLFOX (oxaliplatin, 5-FU, and leucovorin), FOLFIRI (leucovorin calcium+5-FU+irinotecan hydrochloride), 5-FU and leucovorin, CapeOx (capecitabine plus oxaliplatin), or capecitabine alone. In an embodiment, the continuous scoring function is used as follows:

(a) for subjects with stage III colorectal cancer having a poor prognosis as determined by an immune context score (optionally in combination with other diagnostic criteria, such as MMR status), administering a full course of an adjuvant chemotherapy; or (b) for subjects with stage III colorectal cancer having a good prognosis as determined by an immune context score (optionally in combination with other diagnostic criteria, such as MMR status), administering a therapy course that includes post-surgical monitoring and does not include chemotherapy or includes a reduced course of chemotherapy.

In another embodiment, the continuous scoring function may be used in combination with MMR status for selecting stage III colorectal cancer patients to receive an immune checkpoint-directed therapy. Exemplary immune checkpoint-directed therapies include checkpoint inhibitors that target PD-1 (such as pembrolizumab and nivolumab), PD-L1 (such as atezolizumab or durvalumab), CTLA-4 (such as ipilimumab), IDO inhibitors (such as NLG919), etc. In an embodiment, the continuous scoring function is used as follows:

(a) for subjects with stage III colorectal cancer classified as dMMR or $MSI^{high}$ and having a good prognosis as determined by an immune context score, administering a therapy course that includes adjuvant administration of an immune checkpoint inhibitor and optionally includes adjuvant chemotherapy (which may be administered for a reduced duration);

(b) for subjects with stage III colorectal cancer either: (a) classified as dMMR or $MSI^{high}$ and having a poor prognosis as determined by an immune context score, or (b) classified as pMMR or $MSI^{low}$ and having a good prognosis as determined by an immune context score, administering a therapy course that includes adjuvant chemotherapy, optionally including adjuvant administration of an immune checkpoint inhibitor; and (c) for subjects with stage III colorectal cancer classified as pMMR or $MSI^{low}$ and having a poor prognosis as determined by an immune context score, administering a therapy course that includes adjuvant chemotherapy, and does not include an immune checkpoint inhibitor.

In an embodiment, the immune checkpoint-directed therapy is a PD-1 or a PD-L1 directed therapy.

IV.B. Immune context scoring systems

In an embodiment, the continuous scoring function as described herein is implemented by an immune context scoring system. An exemplary immune context scoring system is illustrated at FIG. 2.

The immune context scoring system includes an image analysis system 100. Image analysis system 100 may include one or more computing devices such as desktop computers, laptop computers, tablets, smartphones, servers, application-specific computing devices, or any other type(s) of electronic device(s) capable of performing the techniques and operations described herein. In some embodiments, image analysis system 100 may be implemented as a single device. In other embodiments, image analysis system 100 may be implemented as a combination of two or more devices together achieving the various functionalities discussed herein. For example, image analysis system 100 may include one or more server computers and a one or more client computers communicatively coupled to each other via one or more local-area networks and/or wide-area networks such as the Internet.

Figure 2:
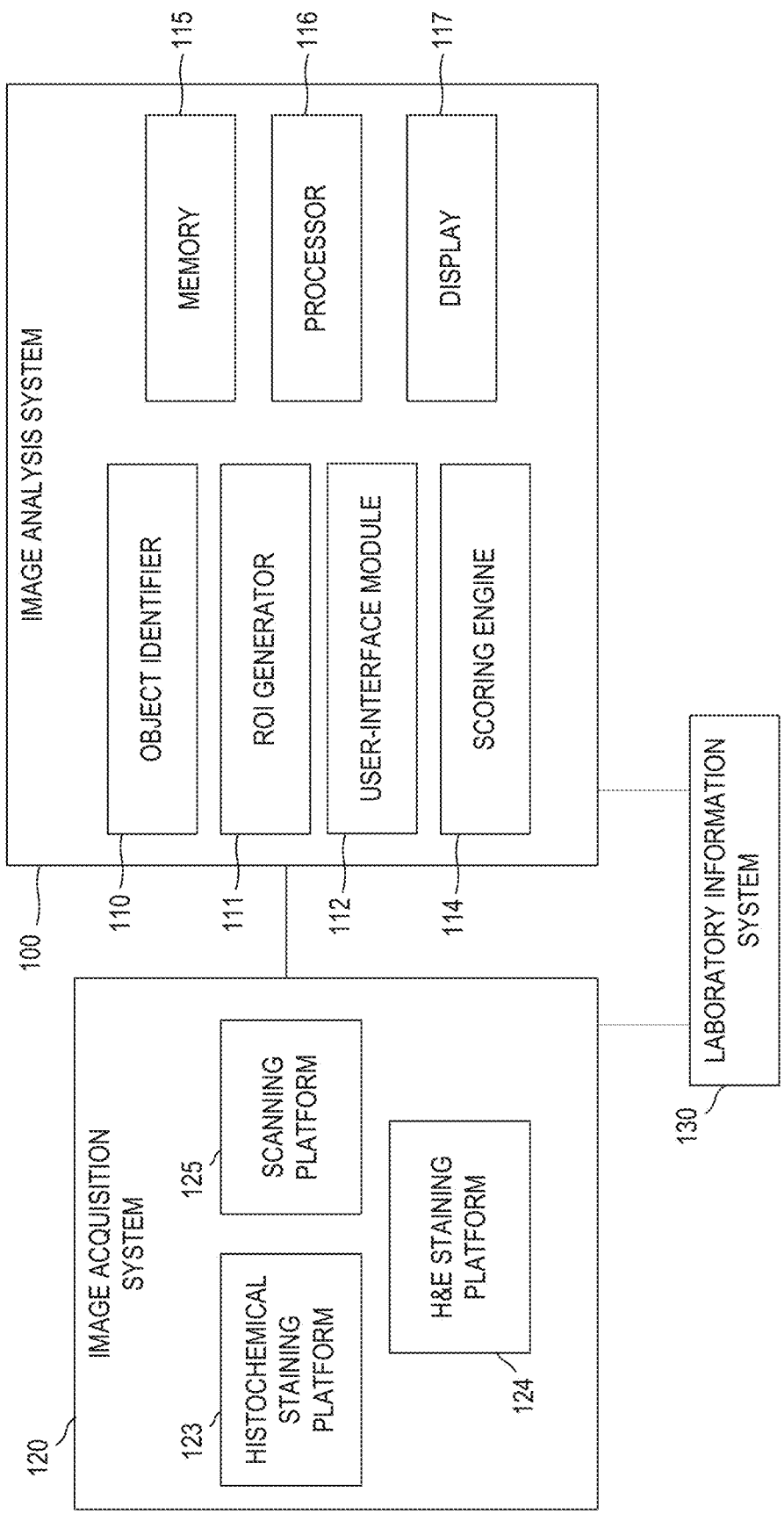
FIG. 2 illustrates an exemplary immune context scoring system as disclosed herein.

As illustrated in FIG. 2, image analysis system 100 may include a memory 116, a processor 117, and a display 118. Memory 116 may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. For brevity purposes memory 116 is depicted in FIG. 2 as a single device, but it is appreciated that memory 116 can also be distributed across two or more devices.

Processor 117 may include one or more processors of any type, such as central processing units (CPUs), graphics processing units (GPUs), special-purpose signal or image processors, field-programmable gate arrays (FPGAs), tensor processing units (TPUs), and so forth. For brevity purposes processor 117 is depicted in FIG. 2 as a single device, but it is appreciated that processor 117 can also be distributed across any number of devices.

Display 118 may be implemented using any suitable technology, such as LCD, LED, OLED, TFT, Plasma, etc. In some implementations, display 118 may be a touch-sensitive display (a touchscreen).

As illustrated in FIG. 2, image analysis system 100 may also include an object identifier 110, a region of interest (ROI) generator 111, a user-interface module 112, and a scoring engine 114. While these modules are depicted in FIG. 2 as standalone modules, it will be evident to persons having ordinary skill in the art that each module may instead be implemented as a number of sub-modules, and that in some embodiments any two or more modules can be combined into a single module. Furthermore, in some embodiments, system 100 may include additional engines and modules (e.g., input devices, networking and communication modules, etc.) not depicted in FIG. 2 for brevity. Furthermore, in some embodiments, some of the blocks depicted in FIG. 2 may be disabled or omitted. As will be discussed in more detail below, the functionality of some or all modules of system 100 can be implemented in hardware, software, firmware, or as any combination thereof. Exemplary commercially-available software packages useful in implementing modules as disclosed herein include VENTANA VIRTUOSO; Definiens TISSUE STUDIO, DEVELOPER XD, and IMAGE MINER; and Visopharm BIOTOPIX, ONCOTOPIX, and STEREOTOPIX software packages.

After acquiring the image, image analysis system 100 may pass the image to an object identifier 110, which functions to identify and mark relevant objects and other features within the image that will later be used for scoring. Object identifier 110 may extract from (or generate for) each image a plurality of image features characterizing the various objects in the image as a well as pixels representing expression of the biomarker(s). The extracted image features may include, for example, texture features such as Haralick features, bag-of-words features and the like. The values of the plurality of image features may be combined into a high-dimensional vector, hereinafter referred to as the "feature vector" characterizing the expression of the biomarker. For example, if M features are extracted for each object and/or pixel, each object and/or pixel can be characterized by an M-dimensional feature vector. The output of object identifier 110 is effectively a map of the image annotating the position of objects and pixels of interest and associating those objects and pixels with a feature vector describing the object or pixels. The features extracted by object identifier 110 include at least features or feature vectors sufficient to distinguish CD3+ cells from CD3− cells in an image histochemically stained with a human CD3 biomarker specific reagent.

The image analysis system 100 may also pass the image to ROI generator 111. ROI generator 111 is used to identify the ROI or ROIs of the image from which the immune context score will be calculated. In cases where the object identifier 110 is not applied to the whole image, the ROI or ROIs generated by the ROI generator 111 may also be used to define a subset of the image on which object identifier 110 is executed.

In one embodiment, ROI generator 111 may be accessed through user-interface module 112. An image of the biomarker-stained sample (or a morphologically-stained serial section of the biomarker-stained sample) is displayed on a graphic user interface of the user interface module 112, and the user annotates one or more region(s) in the image to be considered ROIs. ROI annotation can take a number of forms in this example. For example, the user may manually define the ROI (referred to hereafter as "manual ROI annotation"). In other examples, the ROI generator 111 may assist the user in annotating the ROI (termed, "semi-automated ROI annotation") as described above in section III.F.

In some embodiments, ROI generator 111 may also include a registration function, whereby an ROI annotated in one section of a set of serial sections is automatically transferred to other sections of the set of serial sections. This functionality is especially useful when there are multiple biomarkers being analyzed, or when an H&E-stained serial section is provided along with the biomarker-labeled sections.

Figure 3B:
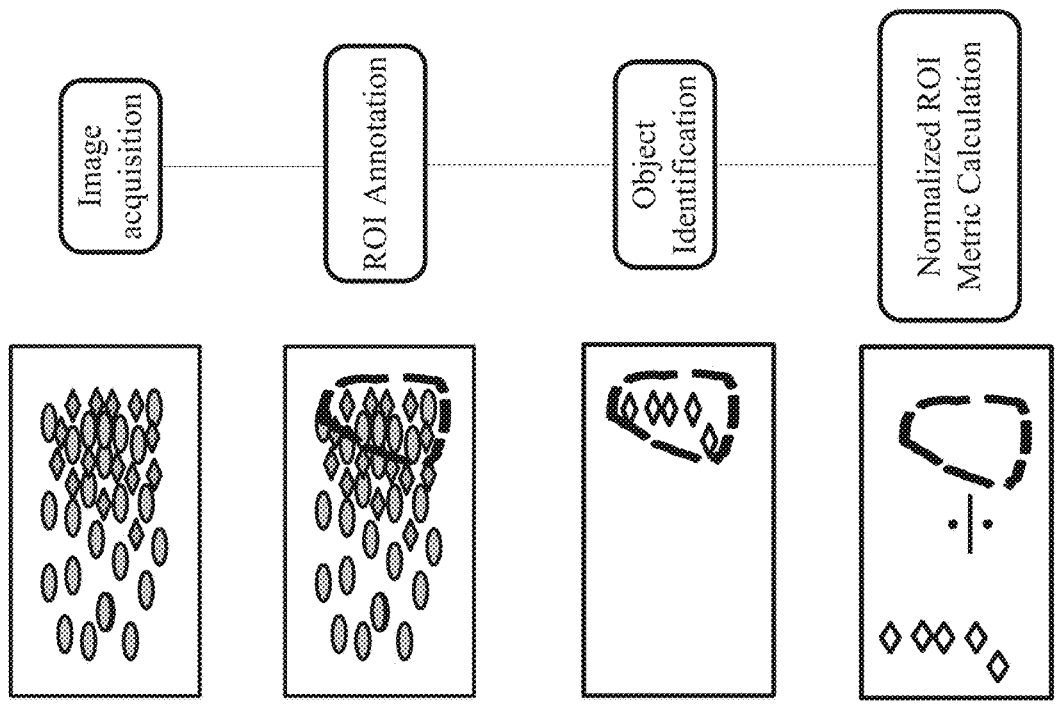
FIG. 3B illustrates an exemplary workflow implemented on an image analysis system as disclosed herein, wherein the object identification function is executed on only the ROI after the ROI generator function is executed.
Figure 3A:
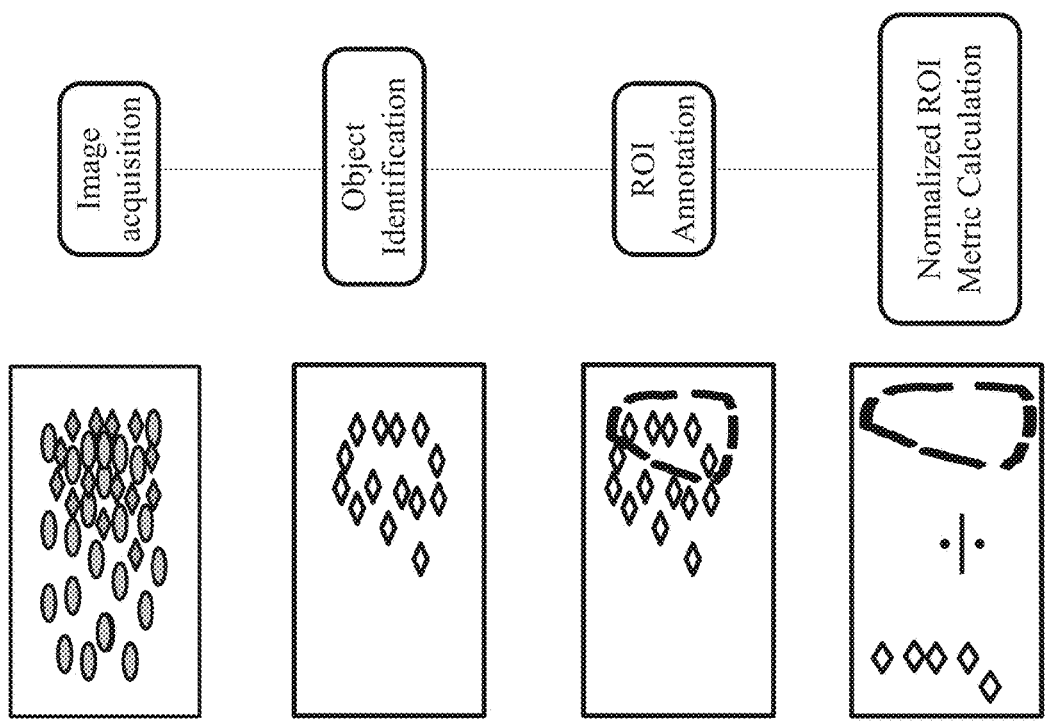
FIG. 3A illustrates an exemplary workflow implemented on an image analysis system as disclosed herein, wherein the object identification function is executed on the whole image before the ROI generator function is executed.

The object identifier 110 and the ROI generator 111 may be implemented in any order. For example, the object identifier 110 may be applied to the entire image first. The positions and features of the identified objects can then be stored and recalled later when the ROI generator 111 is implemented. In such an arrangement, a score can be generated by the scoring engine 113 immediately upon generation of the ROI. Such a workflow is illustrated at FIG. 3A. As can be seen at FIG. 3A, an image is obtained having a mixture of different object (illustrated by dark ovals and dark diamonds). After object identification task is implemented, all diamonds in the image are identified (illustrated by open diamonds). When the ROI is appended to the image (illustrated by the dashed line), only the diamonds located in the ROI region are included in the metric calculation for the ROI. A feature vector is then calculated including the feature metric and any additional metrics used by a continuous scoring function as described below. Alternatively, the ROI generator 111 can be implemented first. In this work flow, the object identifier 110 may be implemented only on the ROI (which minimizes computation time), or it may still be implemented on the whole image (which would allow on-the-fly adjustments without re-running the object identifier 110). Such a workflow is illustrated at FIG. 3B. As can be seen at FIG. 3B, an image is obtained having a mixture of different object (illustrated by dark ovals and dark diamonds). The ROI is appended to the image (illustrated by the dashed line), but no objects have been marked yet. After object identification task is implemented on the ROI, all diamonds in the ROI are identified (illustrated by open diamonds) and included in the feature metric calculation for the ROI. A feature vector is then calculated including the feature metric(s) and any additional metrics used by the continuous scoring function. It may also be possible to implement the object identifier 110 and ROI generator 111 simultaneously.

After both the object identifier 110 and ROI generator 111 have been implemented, a scoring engine 112 is implemented. The scoring engine 112 calculates feature metric(s) for the ROI from at least one ROI metric (such as ROI area or linear length of an ROI edge), relevant metrics for objects in the ROI (such as number CD3+ cells in the ROI), and, if being used, pre-determined maximum and/or minimum cut-offs and/or normalization factors. Where the feature metric is a global metric, the scoring engine 112 may also include a function that overlays a plurality of control regions in the ROI for calculating the CR metric. A ROI feature vector including the calculated feature metrics and any other variable derived from the ROI used by the continuous scoring function, and applies the continuous scoring function to the ROI feature vector.

As depicted in FIG. 2, in some embodiments image analysis system 100 may be communicatively coupled to an image acquisition system 120. Image acquisition system 120 may obtain images of samples and provide those images to image analysis system 100 for analysis and presentation to the user.

Figure 4:
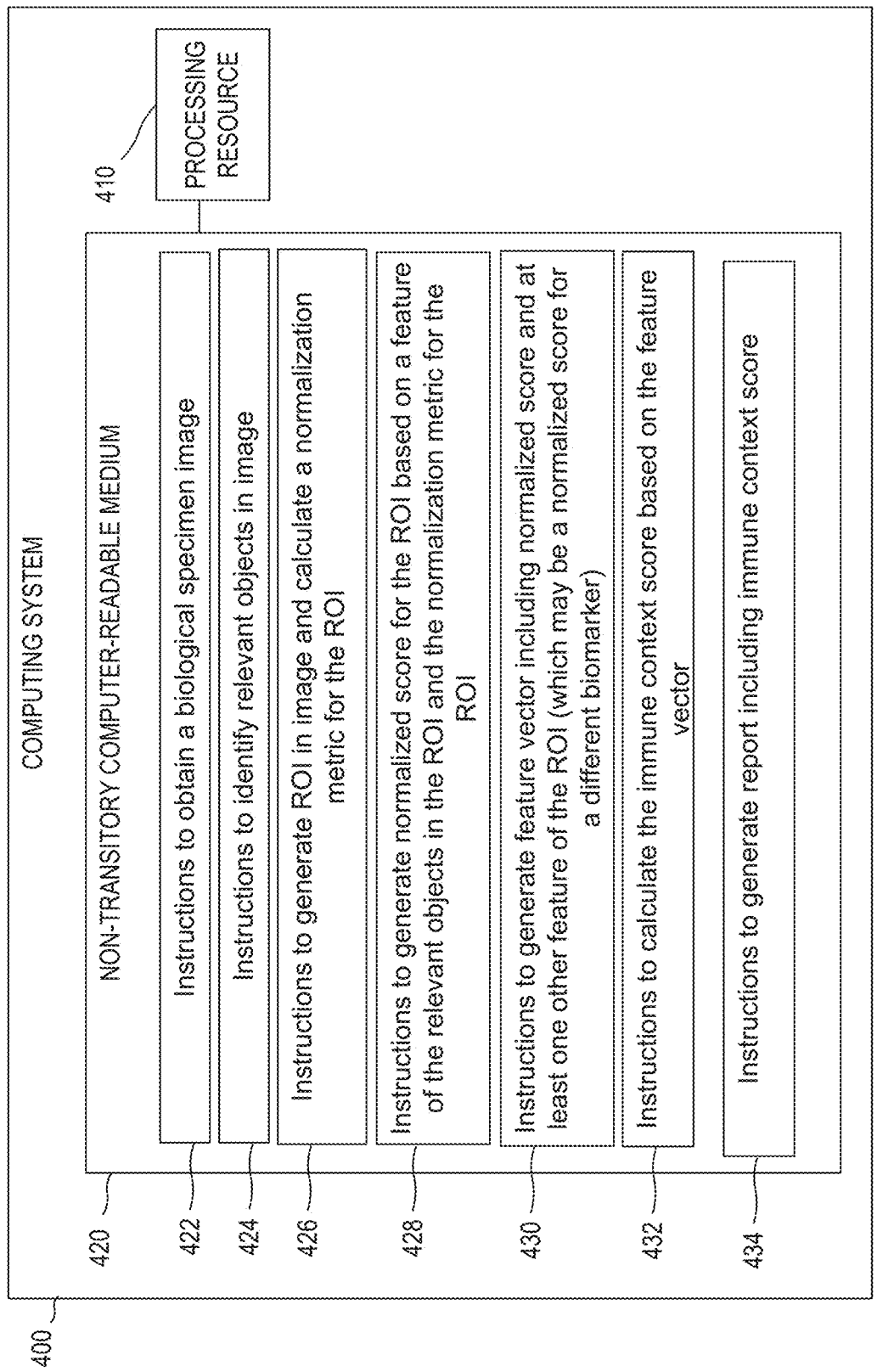
FIG. 4 illustrates an exemplary computing system that may form part of an image analysis system as disclosed herein.

As illustrated in FIG. 4, the image analysis system may include a computing system 400 for implementing the various functions, the computing system 400 comprising a processing resource 410 and a non-transitory computer readable medium 420. The non-transitory computer readable medium 420 includes, for example, instructions to execute function(s) that: obtain a biological specimen image 422; identify relevant objects in the image 424; generate an ROI in the image 426; calculate an ROI metric for the ROI 426; generate a feature metric based on the relevant objects in the ROI, the ROI metric 428, and other optional factors being used, such as normalization factors and/or maximum and/or minimum feature values; generate a feature vector including the feature metric and at least one other feature metric of the sample (which may be, for example, an additional feature metric for a different biomarker) 430; calculate immune context score based on the feature vector 432; and generate a report including the immune context score 434.

Image acquisition system 120 may also include a scanning platform 125 such as a slide scanner that can scan the stained slides at 20*x*, 40*x*, or other magnifications to produce high resolution whole-slide digital images, including for example slide scanners as discussed above at section IV. At a basic level, the typical slide scanner includes at least: (1) a microscope with lens objectives, (2) a light source (such as halogen, light emitting diode, white light, and/or multispectral light sources, depending on the dye), (3) robotics to move glass slides around (or to move the optics around the slide), (4) one or more digital cameras for image capture, (5) a computer and associated software to control the robotics and to manipulate, manage, and view digital slides. Digital data at a number of different X-Y locations (and in some cases, at multiple Z planes) on the slide are captured by the camera's charge-coupled device (CCD), and the images are joined together to form a composite image of the entire scanned surface. Common methods to accomplish this include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image.

A detailed overview of various scanners (both fluorescent and brightfield) can be found at Farahani et al., *Whole slide imaging in pathology: advantages, limitations, and emerging perspectives*, Pathology and Laboratory Medicine Int'l, Vol. 7, p. 23-33 (June 2015), the content of which is incorporated by reference in its entirety. Examples of commercially available slide scanners include: 3DHistech PANORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO and ISCAN HT; and Zeiss AXIO SCAN.Z1. Other exemplary systems and features can be found in, for example, WO2011-049608) or in U.S. Patent Application No. 61/533,114, filed on Sep. 9, 2011, entitled IMAGING SYSTEMS, CASSETTES, AND METHODS OF USING THE SAME the content of which is incorporated by reference in its entirety.

Images generated by scanning platform 125 may be transferred to image analysis system 100 or to a server or database accessible by image analysis system 100. In some embodiments, the images may be transferred automatically via one or more local-area networks and/or wide-area networks. In some embodiments, image analysis system 100 may be integrated with or included in scanning platform 125 and/or other modules of image acquisition system 120, in which case the image may be transferred to image analysis system, e.g., through a memory accessible by both platform 125 an system 120. In some embodiments, image acquisition system 120 may not be communicatively coupled to image analysis system 100, in which case the images may be stored on a non-volatile storage medium of any type (e.g., a flash drive) and downloaded from the medium to image analysis system 100 or to a server or database communicatively coupled thereto. In any of the above examples, image analysis system 100 may obtain an image of a biological sample, where the sample may have been affixed to a slide and stained by histochemical staining platform 123, and where the slide may have been scanned by a slide scanner or another type of scanning platform 125. It is appreciated, however, that in other embodiments, below-described techniques may also be applied to images of biological samples acquired and/or stained through other means.

Image acquisition system 120 may also include an automated histochemical staining platform 123, such as an automated IHC/ISH slide stainer. Automated IHC/ISH slide stainers typically include at least: reservoirs of the various reagents used in the staining protocols, a reagent dispense unit in fluid communication with the reservoir(s) for dispensing reagent to onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, *Overview of Automated Immunohistochemistry*, Arch Pathol Lab Med., Vol. 138, pp. 1578-1582 (2014), incorporated herein by reference in its entirety, describes several specific examples of automated IHC/ISH slide stainers and their various features, including the intelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published patents application Nos. 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be incorporated into the histochemical staining platform 123.

Image acquisition system 120 may also include an automated H&E staining platform 124. Automated systems for performing H&E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH. H&E staining platform 124 is typically used in workflows in which a morphologically-stained serial section of the biomarker-stained section(s) is desired.

The immune context scoring system may further include a laboratory information system (LIS) 130. LIS 130 typically performs one or more functions selected from: recording and tracking processes performed on samples and on slides and images derived from the samples, instructing different components of the immune context scoring system to perform specific processes on the samples, slides, and/or images, and track information about specific reagents applied to samples and or slides (such as lot numbers, expiration dates, volumes dispensed, etc.). LIS 130 usually comprises at least a database containing information about samples; labels associated with samples, slides, and/or image files (such as barcodes (including 1-dimensional barcodes and 2-dimensional barcodes), radio frequency identification (RFID) tags, alpha-numeric codes affixed to the sample, and the like); and a communication device that reads the label on the sample or slide and/or communicates information about the slide between the LIS 130 and the other components of the immune context scoring system. Thus, for example, a communication device could be placed at each of a sample processing station, automated histochemical stainer 123, H&E staining platform 124, and scanning platform 125. When the sample is initially processed into sections, information about the sample (such as patient ID, sample type, processes to be performed on the section(s)) may be entered into the communication device, and a label is created for each section generated from the sample. At each subsequent station, the label is entered into the communication device (such as by scanning a barcode or RFID tag or by manually entering the alpha-numeric code), and the station electronically communicates with the database to, for example, instruct the station or station operator to perform a specific process on the section and/or to record processes being performed on the section. At scanning platform 125, the scanning platform 125 may also encode each image with a computer-readable label or code that correlates back to the section or sample from which the image is derived, such that when the image is sent to the image analysis system 100, image processing steps to be performed may be sent from the database of LIS 130 to the image analysis system and/or image processing steps performed on the image by image analysis system 100 are recorded by database of LIS 130. Commercially available LIS systems useful in the present methods and systems include, for example, VENTANA Vantage Workflow system (Roche).

V. Generation of an Exemplary CD3 Continuous Scoring Function for Stage III Colorectal Cancer V.A. Samples and Sample Staining Formalin-fixed, paraffin embedded tissue samples of 563 stage III colon cancers (dMMR n=278; randomly selected pMMR n=283) from a phase 3 trial of FOLFOX-based adjuvant therapy (N=2665 [dMMR 563, pMMR 2102]) were selected for analysis of CD3+ and CD8+ T-cell densities at the invasive margin (IM) and tumor core (TC). Median follow-up was 6.3 years.

Five 4 μm sections of each FFPE sample were obtained, mounted on a slide, and stained as follows:
1. CD3 negative control (i.e. staining protocol with primary antibody diluent in place of primary antibody)
2. CD3 IHC
3. H&E
4. CD8 IHC
5. CD8 neg. control.

IHC Slides were stained on a VENTANA BenchMark XT IHC/ISH automated slide stainer using OptiView DAB detection The primary antibodies used were CONFIRM anti-CD3 (2GV6) Rabbit Monoclonal Primary Antibody (Ventana Medical Systems, Inc.) and anti-CD8 (SP239) rabbit monoclonal antibody (Spring Bioscience). Slides were counterstained with hematoxylin. H&E slides were stained using a VENTANA SYMPHONY automated slide stainer.

V.B. Image Acquisition, Image Analysis, and Continuous Scoring Function Generation Slides were scanned on a VENTANA ISCAN COREO slide scanner. All image analysis was conducted using a VENTANA VIRTUOSO software suite.

IHC slides were pre-processed to mark CD3+ cells in the CD3-stained slides and CD8+ cells in the CD8-stained slides. A tumor region, an invasive margin, and a tumor core region were annotated by an expert reader, and densities of CD3+ cells and CD8+ cells were obtained.

The density values were normalized by first selecting a maximum meaningful cutoff from visual inspection of the distribution of the measured densities. Because of a right-skewed distribution for both the CD3+ and CD8+ cell densities, a maximum cutoff was chosen to allow meaningful separation of the majority of the results following normalization. Various maximum cutoffs were evaluated to identify the lowest maximum biologically meaningful density cutoff, in increments of 500, which would result in less than 30 subjects being marked above biologically meaningful. Any score above the selected cut point was then assigned a value equal to the cutoff. The reassigned scores were then divided by the cutoff value and multiplied by 100.

Multivariate cox proportional hazard models were fitted using the normalized continuous scores to explore the association between the outcome (OS) and to these scores. Normalized continuous measures were fitted to a weighted model to derive a total score reflective of the probability of recurrence or survival. ROC curves were used to maximize the sensitivity and specificity of the score in predicting outcome (OS) and to derive a cutoff to stratify the cohort into high and low risk bins. Separate cutoffs were selected for pMMR and dMMR patients. Kaplan-Meier curves were generated for the low and high score groups, and a logrank p-value was calculated. The Cox proportional hazard models were then fitted to get the hazard ratio and 95% CI to show the overall effect.

The density of CD3+ and CD8+ T-cells was higher in dMMR vs pMMR tumors (P<0.001), and showed significant heterogeneity among patients in each MMR group. CD3+ IM was consistently the strongest prognostic marker as revealed by backward selection; the other markers did not add further prognostic value. Among dMMR tumors, a lower CD3$^+$ IM density as a continuous variable was independently associated with shorter OS ($P_{adj}$=0.007). Using an optimized cutpoint, 58% (167/278) of dMMR tumors had low CD3+ IM, and these patients had shorter OS v dMMR tumors with high CD3$^+$ IM (Table). Furthermore, OS of dMMR tumors with low CD3$^+$ IM was comparable to the overall pMMR cohort (n=1819; $HR_{adj}$ 1.05). Among pMMR tumors, using an optimized cutpoint, 63% (177/283) had a high CD3$^+$ IM and longer OS versus pMMR tumors with low CD3$^+$ IM (Table 2). Patients with high CD3+ IM pMMR tumors had an OS similar to tumor infiltrating lymphocyte (TIL)-unselected dMMR tumors (P=0.2).

Hazard ratios using CD3 are illustrated in Table 2:

TABLE 2

| | | $HR_{adj}$ | $P_{adj}$ | 5-year OS rate |
|---|---|---|---|---|
| dMMR | High CD3$^+$ IM | Ref | 0.024 | 84% |
| | Low CD3$^+$ IM | 2.09 | | 70% |
| pMMR | High CD3$^+$ IM | 0.56 | 0.091 | 83% |
| | Low CD3$^+$ IM | Ref | | 73% |

CD3+ IM TILs can prognostically stratify patients with stage III colon cancer for overall survival. These findings may indicate that patients with a relatively high density of CD3+ cells in IM may be candidates for reduced or eliminated adjuvant chemotherapy, and may indicate that patients with dMMR and high CD3 may be candidates for receipt of immune checkpoint directed therapies (such as PD-1 or PD-L1 directed therapies), with or without adjuvant chemotherapy.

REFERENCES

1. Anitei et al., *Prognostic and Predictive Values of the Immunoscore in Patients with Rectal Cancer*, Clinical Cancer Res., Vol. 20, Issue 7, pp. 1891-1899 (2014).
2. Chen & Srinivas, *Automatic Lymphocyte Detection in H&E Images with Deep Neural Networks*, arXiv: 1612.03217v1 (submitted 9 Dec. 2016; available at https://arxiv.org/abs/1612.03217).
3. Forrest et al., *Comparison of visual and automated assessment of tumour inflammatory infiltrates in patients with colorectal cancer*, European J. Cancer, Vol. 50, Issue 3, pp. 544-552 (2014).
4. Galon et al., *Towards the introduction of the 'Immunoscore' in the classification of malignant tumours*, J. Pathol., Vol. 232, Issue 2, pp. 199-209 (2014).
5. Galon et al., *Validation of the Immunoscore (IM) as a prognostic marker in stage I/II/III colon cancer: Results of a worldwide consortium-based analysis of 1,336 patients.*, J. Clin. Oncol., Vol. 34, suppl. Abstract No. 3500 (2016) (available at http://meetinglibrary.asco.org/content/168666-176) ("Galon (2016a)").
6. Galon et al., *Validation of the Immunoscore (IM) as a prognostic marker in stage I/II/III colon cancer: Results of a worldwide consortium-based analysis of 1,336 patients.* Powerpoint presentation (2016) (http://meetinglibrary.asco.org/content/123627?media=sl) ("Galon (2016b)").
7. Jass, *Lymphocytic infiltration and survival in rectal cancer*, J. Clin. Pathol., Vol. 39, Issue 6, pp. 585-589 (1986).
8. Jass et al., *A new prognostic classification of rectal cancer*, The Lancet, Vol. 329, Issue 8545, pp. 1303-1306 (1987).
9. Mei et al., *Tumour-infiltrating inflammation and prognosis in colorectal cancer: systematic review and meta-analysis*, British J. Cancer, Vol. 110, pp. 11595-1605 (2014).
10. Pagès et al., *Immune infiltration in human tumors: a prognostic factor that should not be ignored*, Oncogene, Vol. 29, pp. 1093-1102 (2010).

The invention claimed is:

1. A method comprising:
   (a) annotating an invasive margin (IM) or a peri-tumoral (PT) region of interest (ROI) on a digital image of a test sample of a stage III colorectal tumor;
   (b) detecting CD3+ cells in at least a portion of the ROI;
   (c) obtaining a CD3+ cell density within the ROI;
   (d) normalizing the obtained CD3+ density by applying a normalization factor to the obtained CD3+ density;
   (e) applying a continuous scoring function to a feature vector comprising the normalized CD3+ cell density to obtain an immune context score (ICS) for the tumor;
   wherein the ROI is identified in a digital image of a first serial section of the test sample, wherein the first serial section is stained with hematoxylin and eosin, and wherein the ROI is automatically registered to a digital image of at least a second serial section of the test sample, wherein the second serial section is stained with CD3.

2. The method of claim 1, wherein the cell density of (c) is an area cell density obtained by dividing the quantity of the labeled cells in the ROI by the area of the ROI.

3. The method of claim 1, wherein the cell density of (c) is derived from a mean or median area cell density of a plurality of control regions of the ROI.

4. The method of claim 1, wherein the density is a total metric.

5. The method of claim 1, wherein the continuous scoring function is a non-linear function derived from a Cox proportional hazard model.

6. A computer-implemented method comprising causing a computer processor to execute a set of computer-executable functions stored on a memory, the set of computer-executable functions comprising:
   (A) obtaining a digital image of at least one tissue section of a stage III colorectal tumor;
   (B) executing on the digital image a method of claim 1.

7. A method of prognosing a stage III colorectal cancer patient, the method comprising:
   calculating an immune context score (ICS) according to claim 1; and
   prognosing the patient on the basis of the ICS.

8. A system for scoring an immune context of a tissue sample, the system comprising:
   a processor; and
   a memory coupled to the processor, the memory to store computer-executable instructions that, when executed by the processor, cause the processor to perform operations comprising the method of claim 1.

9. The system of claim 8, further comprising a scanner or microscope adapted to capture a digital image of a section of the tissue sample and to communicate the image to the computer apparatus.

10. The system of claim 8, further comprising an automated slide stainer programmed to histochemically stain one or more sections of the tissue sample for the human immune cell marker.

11. The system of claim 10, further comprising an automated hematoxylin and eosin stainer programmed to stain one or more serial sections of the sections stained by the automated slide stainer.

12. The system of claim 8, further comprising a laboratory information system (LIS) for tracking sample and image workflow, the LIS comprising a central database configured to receive and store information related to the tissue sample, the information comprising at least one of the following:
   processing steps to be carried out on the tumor tissue sample,
   processing steps to be carried out on digital images of sections of the tumor tissue sample, and
   processing history of the tumor tissue sample and digital images.

13. A non-transitory computer readable storage medium for storing computer-executable instructions that are executed by a processor to perform operations, the operations comprising the method of claim 1.

14. A method of treating a subject having a stage III colorectal cancer, said method comprising:
   (a) obtaining an immune context score (ICS) for the colorectal tumor of the subject according to a method of claim 1; and
   (b) selecting a treatment for the subject based upon the ICS.

15. The method of claim 14, wherein:
   (c1) if the ICS is indicative of a poor prognosis, selecting a treatment comprising a full course of an adjuvant chemotherapy; and
   (c2) if the ICS is indicative of a good prognosis, selecting a treatment comprising a reduced course of an adjuvant chemotherapy or that does not comprise an adjuvant chemotherapy.

16. The method of claim 14, wherein:
   (c1) if the tumor has a dMMR or $MST^{high}$ status and the ICS is indicative of a good prognosis, selecting a treatment comprising a checkpoint inhibitor-directed therapy; and
   (c2) if the tumor has a dMMR or $MST^{high}$ status and the ICS is indicative of a poor prognosis, selecting a treatment comprising an adjuvant chemotherapy;
   (c3) if the tumor has a pMMR or $MSI^{low}$ status and the ICS is indicative of a good prognosis, selecting a treatment comprising an adjuvant chemotherapy; and
   (c4) if the tumor has a pMMR or $MSI^{low}$ status and the ICS is indicative of a poor prognosis, selecting a treatment comprising an adjuvant chemotherapy without a checkpoint inhibitor-directed therapy.

17. The method of claim 16, wherein (c1) and (c3) comprise a reduced course of adjuvant chemotherapy.

18. The method of claim 16, wherein (c1) and (c3) do not comprise adjuvant chemotherapy.

19. The method of claim 16, wherein (c2) and (c4) comprise a full course of adjuvant chemotherapy.

20. The method of claim 16, wherein the checkpoint inhibitor-directed therapy comprises a PD-1-directed therapy.

21. The method of claim 16, wherein the checkpoint inhibitor-directed therapy comprises a PD-L1-directed therapy.

22. The method of claim 16, wherein:
   in step (c1) the treatment further comprises an adjuvant chemotherapy,
   in step (c2) the treatment further comprises a checkpoint inhibitor-directed therapy,
   in step (c3) the treatment further comprises a checkpoint inhibitor-directed therapy.

23. The method of claim 14, wherein the method comprises providing a data base containing a plurality of ICS values having treatments assigned thereto, wherein (c) comprises automatically requesting from the database the treatment assigned to the ICS for the colorectal tumor of the subject.

24. The method of claim 23, wherein the data base contains a plurality of ICS ranges, each ICS range having at least one treatment assigned thereto.

25. The method of claim 23, wherein the database contains at least one lookup-table.

26. The method of claim 14, wherein (c) comprises using at least one self-learning algorithm for selecting the treatment.

27. The method of claim 14, wherein (c) comprises one or more of: storing the selected treatment on a non-transitory computer-readable medium; displaying the selected treatment on a display device; electronically transferring the selected treatment via at least one electronic interface.

28. The method of claim 14, wherein the method further comprises:
   obtaining a mismatch repair (MMR) status or microsatellite instability (MSI) status of the colorectal tumor,
   wherein the selecting the treatment for the subject is further based upon the mismatch repair status.

29. A method for selecting a treatment for a subject having a stage III colorectal cancer, said method comprising:
   (a) obtaining an immune context score (ICS) for the colorectal tumor of the subject according to a method of claim 1; and
   (b) selecting a treatment for the subject based upon the ICS.

30. The method of claim 29, wherein the method further comprises:
   obtaining a mismatch repair (MMR) status or microsatellite instability (MSI) status of the colorectal tumor,
   wherein the selecting the treatment for the subject is further based upon the mismatch repair status.

31. The method according to claim 1, wherein the method is carried out by using a computer or a computer network.

32. The method according to claim 31, wherein the digital image is stored on a data carrier.

33. The method of claim 31, wherein, in (a), the annotation of the region of interest is performed by using an automatic pattern recognition algorithm.

34. The method according to claim 1, wherein, in (b), the detecting of the $CD3^+$ cells is performed by using an automatic pattern recognition algorithm.

35. The method according to claim 1, wherein, in (c), the cell density is obtained by using an automatic counting algorithm.

36. The method according to claim 1, wherein the immune context score (ICS) for the tumor is one or more of: stored on a non-transitory computer-readable medium; displayed on a display device; electronically transferred via at least one electronic interface.

37. A non-transitory computer program comprising instructions which, when the non-transitory computer program is executed by a computer or a computer network, cause the computer or computer network to carry out the method to claim 1.

38. A data processing apparatus comprising a non-transitory computer readable medium or computer program for carrying out the method according to claim 1.

39. A method comprising:
(a) annotating a first region of interest (ROI) on a digital image of a tumor tissue section, the first ROI comprising an invasive margin (IM) region of the tumor;
(b) calculating a feature vector for the first ROI, the feature vector including at least a density of human $CD3^+$ cells in the first ROI;
(c) normalizing the density of the human $CD3^+$ cells in the first ROI by applying a normalization factor to the density of the human $CD3^+$ cells in the first ROI; and
(d) applying a continuous scoring function to the calculated feature vector to determine an immune context score (ICS) for the tissue section;
   wherein the first ROI of (a) is annotated on a digital image of a first serial section of the sample, the first serial section being stained with hematoxylin and eosin (H&E); and
   the feature vector calculation of (b) comprises:
      registering the first ROI to a digital image of a second serial section of the sample, the second serial section being histochemically stained for human CD3; and
      calculating the density of human CD3+ cells from the first ROI registered to the digital image of the second serial section.

40. The method of claim 39, wherein multiple first ROIs are annotated, specifically automatically, wherein at least one ROI includes a portion of a TC region and a separate ROI includes a portion of the IM region.

41. The method of claim 39, wherein the first ROI encompasses a portion of both the TC and IM regions.

42. The method of claim 41, wherein a single first ROI is annotated, specifically automatically, the single first ROI encompassing a portion of both the TC and IM regions.

43. The method of claim 1, wherein the first ROI is a PT ROI.

44. The method of claim 1, wherein the density of human CD3+ cells is selected from the group consisting of:

an area density of cells expressing human CD3 within the ROI, and a linear density of cells expressing human CD3.

45. The method of claim 39, wherein the feature vector consists essentially of a density of CD3+ cells in the IM region or the PT region.

46. The method according to claim 39, wherein, in (b), the detecting of the $CD3^+$ cells is performed by using an automatic pattern recognition algorithm.

* * * * *

SEQUENCE LISTING

<160> NUMBER OF SEQ ID NOS: 18

<210> SEQ ID NO 1
<211> LENGTH: 182
<212> TYPE: PRT
<213> ORGANISM: Homo sapiens

<400> SEQUENCE: 1

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
        50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95
```

```
Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 2
<211> LENGTH: 171
<212> TYPE: PRT
<213> ORGANISM: Homo sapiens

<400> SEQUENCE: 2

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 3
<211> LENGTH: 207
<212> TYPE: PRT
<213> ORGANISM: Homo sapiens

<400> SEQUENCE: 3

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60
```

```
Asn Ile Gly Gly Asp Glu Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                 85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205

<210> SEQ ID NO 4
<211> LENGTH: 164
<212> TYPE: PRT
<213> ORGANISM: Homo sapiens

<400> SEQUENCE: 4

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 5
<211> LENGTH: 235
<212> TYPE: PRT
<213> ORGANISM: Homo sapiens

<400> SEQUENCE: 5

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
```

```
            20                  25                  30
Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 6
<211> LENGTH: 210
<212> TYPE: PRT
<213> ORGANISM: Homo sapiens

<400> SEQUENCE: 6

Met Arg Pro Arg Leu Trp Leu Leu Leu Ala Ala Gln Leu Thr Val Leu
 1               5                  10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
 50                  55                  60

Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160
```

-continued

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Phe
        195                 200                 205

Tyr Lys
    210

<210> SEQ ID NO 7
<211> LENGTH: 223
<212> TYPE: PRT
<213> ORGANISM: Homo sapiens

<400> SEQUENCE: 7

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 8
<211> LENGTH: 431
<212> TYPE: PRT
<213> ORGANISM: Homo sapiens

<400> SEQUENCE: 8

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
 50                  55                  60

Pro Pro Ser Gln Leu Gln Leu Pro Thr Leu Pro Leu Val Met Val Ala
 65                  70                  75                  80

Pro Ser Gly Ala Arg Leu Gly Pro Leu Pro His Leu Gln Ala Leu Leu
                 85                  90                  95

Gln Asp Arg Pro His Phe Met His Gln Leu Ser Thr Val Asp Ala His
                100                 105                 110

Ala Arg Thr Pro Val Leu Gln Val His Pro Leu Glu Ser Pro Ala Met
            115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430

<210> SEQ ID NO 9
<211> LENGTH: 288
<212> TYPE: PRT
<213> ORGANISM: Homo sapiens

<400> SEQUENCE: 9

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 10
<211> LENGTH: 290
<212> TYPE: PRT
<213> ORGANISM: Homo sapiens

<400> SEQUENCE: 10

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn

```
            85                  90                  95
Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                    165                 170                 175

Gly Lys Thr Thr Thr Thr Asn Ser Lys Arg Glu Glu Lys Leu Phe Asn
                    180                 185                 190

Val Thr Ser Thr Leu Arg Ile Asn Thr Thr Thr Asn Glu Ile Phe Tyr
                    195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                    245                 250                 255

Phe Ile Phe Arg Leu Arg Lys Gly Arg Met Met Asp Val Lys Lys Cys
                    260                 265                 270

Gly Ile Gln Asp Thr Asn Ser Lys Lys Gln Ser Asp Thr His Leu Glu
                    275                 280                 285

Glu Thr
        290

<210> SEQ ID NO 11
<211> LENGTH: 273
<212> TYPE: PRT
<213> ORGANISM: Homo sapiens

<400> SEQUENCE: 11

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                    85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
        130                 135                 140

Ala Thr Gly Tyr Pro Leu Ala Glu Val Ser Trp Pro Asn Val Ser Val
145                 150                 155                 160
```

```
Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
            245                 250                 255

Thr Thr Lys Arg Pro Val Thr Thr Thr Lys Arg Glu Val Asn Ser Ala
            260                 265                 270

Ile

<210> SEQ ID NO 12
<211> LENGTH: 301
<212> TYPE: PRT
<213> ORGANISM: Homo sapiens

<400> SEQUENCE: 12

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255
```

```
Gly Ile Arg Ser Glu Glu Asn Ile Tyr Thr Ile Glu Glu Asn Val Tyr
                260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
        290                 295                 300

<210> SEQ ID NO 13
<211> LENGTH: 525
<212> TYPE: PRT
<213> ORGANISM: Homo sapiens

<400> SEQUENCE: 13

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335
```

```
Leu Gln Glu Gln Gln Leu Asn Ala Thr Val Thr Leu Ala Ile Ile Thr
                340                 345                 350
Val Thr Pro Lys Ser Phe Gly Ser Pro Gly Ser Leu Gly Lys Leu Leu
            355                 360                 365
Cys Glu Val Thr Pro Val Ser Gly Gln Glu Arg Phe Val Trp Ser Ser
370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
                405                 410                 415
Gly Glu Arg Leu Leu Gly Ala Ala Val Tyr Phe Thr Glu Leu Ser Ser
            420                 425                 430
Pro Gly Ala Gln Arg Ser Gly Arg Ala Pro Gly Ala Leu Pro Ala Gly
        435                 440                 445
His Leu Leu Leu Phe Leu Ile Leu Gly Val Leu Ser Leu Leu Leu Leu
    450                 455                 460
Val Thr Gly Ala Phe Gly Phe His Leu Trp Arg Arg Gln Trp Arg Pro
465                 470                 475                 480
Arg Arg Phe Ser Ala Leu Glu Gln Gly Ile His Pro Pro Gln Ala Gln
                485                 490                 495
Ser Lys Ile Glu Glu Leu Glu Gln Glu Pro Glu Pro Glu Pro Glu Pro
            500                 505                 510
Glu Pro Glu Pro Glu Pro Glu Pro Glu Gln Leu
        515                 520                 525

<210> SEQ ID NO 14
<211> LENGTH: 403
<212> TYPE: PRT
<213> ORGANISM: Homo sapiens

<400> SEQUENCE: 14

Met Ala His Ala Met Glu Asn Ser Trp Thr Ile Ser Lys Glu Tyr His
1               5                   10                  15
Ile Asp Glu Glu Val Gly Phe Ala Leu Pro Asn Pro Gln Glu Asn Leu
            20                  25                  30
Pro Asp Phe Tyr Asn Asp Trp Met Phe Ile Ala Lys His Leu Pro Asp
        35                  40                  45
Leu Ile Glu Ser Gly Gln Leu Arg Glu Arg Val Glu Lys Leu Asn Met
    50                  55                  60
Leu Ser Ile Asp His Leu Thr Asp His Lys Ser Gln Arg Leu Ala Arg
65                  70                  75                  80
Leu Val Leu Gly Cys Ile Thr Met Ala Tyr Val Trp Gly Lys Gly His
                85                  90                  95
Gly Asp Val Arg Lys Val Leu Pro Arg Asn Ile Ala Val Pro Tyr Cys
            100                 105                 110
Gln Leu Ser Lys Lys Leu Glu Leu Pro Pro Ile Leu Val Tyr Ala Asp
        115                 120                 125
Cys Val Leu Ala Asn Trp Lys Lys Lys Asp Pro Asn Lys Pro Leu Thr
    130                 135                 140
Tyr Glu Asn Met Asp Val Leu Phe Ser Phe Arg Asp Gly Asp Cys Ser
145                 150                 155                 160
Lys Gly Phe Phe Leu Val Ser Leu Leu Val Glu Ile Ala Ala Ala Ser
                165                 170                 175
Ala Ile Lys Val Ile Pro Thr Val Phe Lys Ala Met Gln Met Gln Glu
```

```
            180                 185                 190
Arg Asp Thr Leu Leu Lys Ala Leu Leu Glu Ile Ala Ser Cys Leu Glu
            195                 200                 205

Lys Ala Leu Gln Val Phe His Gln Ile His Asp His Val Asn Pro Lys
        210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
            245                 250                 255

Lys Glu Phe Ala Gly Gly Ser Ala Gly Gln Ser Ser Val Phe Gln Cys
        260                 265                 270

Phe Asp Val Leu Leu Gly Ile Gln Gln Thr Ala Gly Gly His Ala
    275                 280                 285

Ala Gln Phe Leu Gln Asp Met Arg Arg Tyr Met Pro Pro Ala His Arg
        290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
            325                 330                 335

Lys Ala Leu Val Ser Leu Arg Ser Tyr His Leu Gln Ile Val Thr Lys
        340                 345                 350

Tyr Ile Leu Ile Pro Ala Ser Gln Gln Pro Lys Glu Asn Lys Thr Ser
    355                 360                 365

Glu Asp Pro Ser Lys Leu Glu Ala Lys Gly Thr Gly Thr Asp Leu
        370                 375                 380

Met Asn Phe Leu Lys Thr Val Arg Ser Thr Thr Glu Lys Ser Leu Leu
385                 390                 395                 400

Lys Glu Gly

<210> SEQ ID NO 15
<211> LENGTH: 862
<212> TYPE: PRT
<213> ORGANISM: Homo sapiens

<400> SEQUENCE: 15

Met Glu Arg Ala Glu Ser Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Asn Phe
65              70                  75                  80

Glu Gly Leu Thr Leu Lys His His Thr Ser Lys Ile Gln Glu Phe Ala
            85                  90                  95

Asp Leu Thr Gln Val Glu Thr Phe Gly Phe Arg Gly Glu Ala Leu Ser
        100                 105                 110

Ser Leu Cys Ala Leu Ser Asp Val Thr Ile Ser Thr Cys His Ala Ser
    115                 120                 125

Ala Lys Val Gly Thr Arg Leu Met Phe Asp His Asn Gly Lys Ile Ile
130                 135                 140

Gln Lys Thr Pro Tyr Pro Arg Pro Arg Gly Thr Thr Val Ser Val Gln
```

-continued

```
        145                 150                 155                 160
Gln Leu Phe Ser Thr Leu Pro Val Arg His Lys Glu Phe Gln Arg Asn
                165                 170                 175
Ile Lys Lys Glu Tyr Ala Lys Met Val Gln Val Leu His Ala Tyr Cys
                180                 185                 190
Ile Ile Ser Ala Gly Ile Arg Val Ser Cys Thr Asn Gln Leu Gly Gln
                195                 200                 205
Gly Lys Arg Gln Pro Val Val Cys Thr Gly Ser Pro Ser Ile Lys
        210                 215                 220
Glu Asn Ile Gly Ser Val Phe Gly Gln Lys Gln Leu Gln Ser Leu Ile
225                 230                 235                 240
Pro Phe Val Gln Leu Pro Ser Asp Ser Val Cys Glu Glu Tyr Gly
                245                 250                 255
Leu Ser Cys Ser Asp Ala Leu His Asn Leu Phe Tyr Ile Ser Gly Phe
                260                 265                 270
Ile Ser Gln Cys Thr His Gly Val Gly Arg Ser Ser Thr Asp Arg Gln
                275                 280                 285
Phe Phe Phe Ile Asn Arg Arg Pro Cys Asp Pro Ala Lys Val Cys Arg
        290                 295                 300
Leu Val Asn Glu Val Tyr His Met Tyr Asn Arg His Gln Tyr Pro Phe
305                 310                 315                 320
Val Val Leu Asn Ile Ser Val Asp Ser Glu Cys Val Asp Ile Asn Val
                325                 330                 335
Thr Pro Asp Lys Arg Gln Ile Leu Leu Gln Glu Glu Lys Leu Leu Leu
                340                 345                 350
Ala Val Leu Lys Thr Ser Leu Ile Gly Met Phe Asp Ser Asp Val Asn
                355                 360                 365
Lys Leu Asn Val Ser Gln Gln Pro Leu Leu Asp Val Glu Gly Asn Leu
        370                 375                 380
Ile Lys Met His Ala Ala Asp Leu Glu Lys Pro Met Val Glu Lys Gln
385                 390                 395                 400
Asp Gln Ser Pro Ser Leu Arg Thr Gly Glu Glu Lys Lys Asp Val Ser
                405                 410                 415
Ile Ser Arg Leu Arg Glu Ala Phe Ser Leu Arg His Thr Thr Glu Asn
                420                 425                 430
Lys Pro His Ser Pro Lys Thr Pro Glu Pro Arg Arg Ser Pro Leu Gly
        435                 440                 445
Gln Lys Arg Gly Met Leu Ser Ser Ser Thr Ser Gly Ala Ile Ser Asp
        450                 455                 460
Lys Gly Val Leu Arg Pro Gln Lys Glu Ala Val Ser Ser His Gly
465                 470                 475                 480
Pro Ser Asp Pro Thr Asp Arg Ala Glu Val Lys Asp Ser Gly His
                485                 490                 495
Gly Ser Thr Ser Val Asp Ser Glu Gly Phe Ser Ile Pro Asp Thr Gly
                500                 505                 510
Ser His Cys Ser Ser Glu Tyr Ala Ala Ser Ser Pro Gly Asp Arg Gly
        515                 520                 525
Ser Gln Glu His Val Asp Ser Gln Glu Lys Ala Pro Lys Thr Asp Asp
        530                 535                 540
Ser Phe Ser Asp Val Asp Cys His Ser Asn Gln Glu Asp Thr Gly Cys
545                 550                 555                 560
Lys Phe Arg Val Leu Pro Gln Pro Thr Asn Leu Ala Thr Pro Asn Thr
                565                 570                 575
```

```
Lys Arg Phe Lys Lys Glu Ile Leu Ser Ser Ser Asp Ile Cys Gln
            580                 585                 590
Lys Leu Val Asn Thr Gln Asp Met Ser Ala Ser Gln Val Asp Val Ala
        595                 600                 605
Val Lys Ile Asn Lys Lys Val Val Pro Leu Asp Phe Ser Met Ser Ser
610                 615                 620
Leu Ala Lys Arg Ile Lys Gln Leu His His Glu Ala Gln Gln Ser Glu
625                 630                 635                 640
Gly Glu Gln Asn Tyr Arg Lys Phe Arg Ala Lys Ile Cys Pro Gly Glu
                645                 650                 655
Asn Gln Ala Ala Glu Asp Glu Leu Arg Lys Glu Ile Ser Lys Thr Met
            660                 665                 670
Phe Ala Glu Met Glu Ile Ile Gly Gln Phe Asn Leu Gly Phe Ile Ile
        675                 680                 685
Thr Lys Leu Asn Glu Asp Ile Phe Ile Val Asp Gln His Ala Thr Asp
690                 695                 700
Glu Lys Tyr Asn Phe Glu Met Leu Gln Gln His Thr Val Leu Gln Gly
705                 710                 715                 720
Gln Arg Leu Ile Ala Pro Gln Thr Leu Asn Leu Thr Ala Val Asn Glu
                725                 730                 735
Ala Val Leu Ile Glu Asn Leu Glu Ile Phe Arg Lys Asn Gly Phe Asp
            740                 745                 750
Phe Val Ile Asp Glu Asn Ala Pro Val Thr Glu Arg Ala Lys Leu Ile
        755                 760                 765
Ser Leu Pro Thr Ser Lys Asn Trp Thr Phe Gly Pro Gln Asp Val Asp
770                 775                 780
Glu Leu Ile Phe Met Leu Ser Asp Ser Pro Gly Val Met Cys Arg Pro
785                 790                 795                 800
Ser Arg Val Lys Gln Met Phe Ala Ser Arg Ala Cys Arg Lys Ser Val
                805                 810                 815
Met Ile Gly Thr Ala Leu Asn Thr Ser Glu Met Lys Lys Leu Ile Thr
            820                 825                 830
His Met Gly Glu Met Asp His Pro Trp Asn Cys Pro His Gly Arg Pro
        835                 840                 845
Thr Met Arg His Ile Ala Asn Leu Gly Val Ile Ser Gln Asn
850                 855                 860

<210> SEQ ID NO 16
<211> LENGTH: 756
<212> TYPE: PRT
<213> ORGANISM: Homo sapiens

<400> SEQUENCE: 16

Met Ser Phe Val Ala Gly Val Ile Arg Arg Leu Asp Glu Thr Val Val
1               5                   10                  15
Asn Arg Ile Ala Ala Gly Glu Val Ile Gln Arg Pro Ala Asn Ala Ile
            20                  25                  30
Lys Glu Met Ile Glu Asn Cys Leu Asp Ala Lys Ser Thr Ser Ile Gln
        35                  40                  45
Val Ile Val Lys Glu Gly Gly Leu Lys Leu Ile Gln Ile Gln Asp Asn
    50                  55                  60
Gly Thr Gly Ile Arg Lys Glu Asp Leu Asp Ile Val Cys Glu Arg Phe
65                  70                  75                  80
Thr Thr Ser Lys Leu Gln Ser Phe Glu Asp Leu Ala Ser Ile Ser Thr
```

-continued

```
                85                  90                  95
Tyr Gly Phe Arg Gly Glu Ala Leu Ala Ser Ile Ser His Val Ala His
            100                 105                 110
Val Thr Ile Thr Thr Lys Thr Ala Asp Gly Lys Cys Ala Tyr Arg Ala
            115                 120                 125
Ser Tyr Ser Asp Gly Lys Leu Lys Ala Pro Lys Pro Cys Ala Gly
        130                 135                 140
Asn Gln Gly Thr Gln Ile Thr Val Glu Asp Leu Phe Tyr Asn Ile Ala
145                 150                 155                 160
Thr Arg Arg Lys Ala Leu Lys Asn Pro Ser Glu Glu Tyr Gly Lys Ile
                165                 170                 175
Leu Glu Val Val Gly Arg Tyr Ser Val His Asn Ala Gly Ile Ser Phe
            180                 185                 190
Ser Val Lys Lys Gln Gly Glu Thr Val Ala Asp Val Arg Thr Leu Pro
            195                 200                 205
Asn Ala Ser Thr Val Asp Asn Ile Arg Ser Ile Phe Gly Asn Ala Val
        210                 215                 220
Ser Arg Glu Leu Ile Glu Ile Gly Cys Glu Asp Lys Thr Leu Ala Phe
225                 230                 235                 240
Lys Met Asn Gly Tyr Ile Ser Asn Ala Asn Tyr Ser Val Lys Lys Cys
                245                 250                 255
Ile Phe Leu Leu Phe Ile Asn His Arg Leu Val Glu Ser Thr Ser Leu
            260                 265                 270
Arg Lys Ala Ile Glu Thr Val Tyr Ala Ala Tyr Leu Pro Lys Asn Thr
            275                 280                 285
His Pro Phe Leu Tyr Leu Ser Leu Glu Ile Ser Pro Gln Asn Val Asp
        290                 295                 300
Val Asn Val His Pro Thr Lys His Glu Val His Phe Leu His Glu Glu
305                 310                 315                 320
Ser Ile Leu Glu Arg Val Gln Gln His Ile Glu Ser Lys Leu Leu Gly
                325                 330                 335
Ser Asn Ser Ser Arg Met Tyr Phe Thr Gln Thr Leu Leu Pro Gly Leu
            340                 345                 350
Ala Gly Pro Ser Gly Glu Met Val Lys Ser Thr Thr Ser Leu Thr Ser
            355                 360                 365
Ser Ser Thr Ser Gly Ser Ser Asp Lys Val Tyr Ala His Gln Met Val
        370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
            420                 425                 430
Glu Leu Pro Ala Pro Ala Glu Val Ala Ala Lys Asn Gln Ser Leu Glu
            435                 440                 445
Gly Asp Thr Thr Lys Gly Thr Ser Glu Met Ser Glu Lys Arg Gly Pro
        450                 455                 460
Thr Ser Ser Asn Pro Arg Lys Arg His Arg Glu Asp Ser Asp Val Glu
465                 470                 475                 480
Met Val Glu Asp Asp Ser Arg Lys Glu Met Thr Ala Ala Cys Thr Pro
                485                 490                 495
Arg Arg Arg Ile Ile Asn Leu Thr Ser Val Leu Ser Leu Gln Glu Glu
            500                 505                 510
```

```
Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Asp Gly Pro Lys Glu Gly Leu Ala
    595                 600                 605

Glu Tyr Ile Val Glu Phe Leu Lys Lys Ala Glu Met Leu Ala Asp
    610                 615                 620

Tyr Phe Ser Leu Glu Ile Asp Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Lys Glu Cys
            660                 665                 670

Phe Glu Ser Leu Ser Lys Glu Cys Ala Met Phe Tyr Ser Ile Arg Lys
    675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
    755

<210> SEQ ID NO 17
<211> LENGTH: 934
<212> TYPE: PRT
<213> ORGANISM: Homo sapiens

<400> SEQUENCE: 17

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
```

-continued

```
                115                 120                 125
Ser Gln Phe Glu Asp Ile Leu Phe Gly Asn Asn Asp Met Ser Ala Ser
            130                 135                 140
Ile Gly Val Val Gly Val Lys Met Ser Ala Val Asp Gly Gln Arg Gln
145                 150                 155                 160
Val Gly Val Gly Tyr Val Asp Ser Ile Gln Arg Lys Leu Gly Leu Cys
                165                 170                 175
Glu Phe Pro Asp Asn Asp Gln Phe Ser Asn Leu Glu Ala Leu Leu Ile
            180                 185                 190
Gln Ile Gly Pro Lys Glu Cys Val Leu Pro Gly Gly Glu Thr Ala Gly
            195                 200                 205
Asp Met Gly Lys Leu Arg Gln Ile Ile Gln Arg Gly Gly Ile Leu Ile
            210                 215                 220
Thr Glu Arg Lys Lys Ala Asp Phe Ser Thr Lys Asp Ile Tyr Gln Asp
225                 230                 235                 240
Leu Asn Arg Leu Leu Lys Gly Lys Gly Glu Gln Met Asn Ser Ala
                245                 250                 255
Val Leu Pro Glu Met Glu Asn Gln Val Ala Val Ser Ser Leu Ser Ala
            260                 265                 270
Val Ile Lys Phe Leu Glu Leu Leu Ser Asp Asp Ser Asn Phe Gly Gln
            275                 280                 285
Phe Glu Leu Thr Thr Phe Asp Phe Ser Gln Tyr Met Lys Leu Asp Ile
290                 295                 300
Ala Ala Val Arg Ala Leu Asn Leu Phe Gln Gly Ser Val Glu Asp Thr
305                 310                 315                 320
Thr Gly Ser Gln Ser Leu Ala Ala Leu Leu Asn Lys Cys Lys Thr Pro
                325                 330                 335
Gln Gly Gln Arg Leu Val Asn Gln Trp Ile Lys Gln Pro Leu Met Asp
            340                 345                 350
Lys Asn Arg Ile Glu Glu Arg Leu Asn Leu Val Glu Ala Phe Val Glu
            355                 360                 365
Asp Ala Glu Leu Arg Gln Thr Leu Gln Glu Asp Leu Leu Arg Arg Phe
            370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                405                 410                 415
Val Ile Gln Ala Leu Glu Lys His Glu Gly Lys His Gln Lys Leu Leu
            420                 425                 430
Leu Ala Val Phe Val Thr Pro Leu Thr Asp Leu Arg Ser Asp Phe Ser
            435                 440                 445
Lys Phe Gln Glu Met Ile Glu Thr Thr Leu Asp Met Asp Gln Val Glu
            450                 455                 460
Asn His Glu Phe Leu Val Lys Pro Ser Phe Asp Pro Asn Leu Ser Glu
465                 470                 475                 480
Leu Arg Glu Ile Met Asn Asp Leu Glu Lys Lys Met Gln Ser Thr Leu
                485                 490                 495
Ile Ser Ala Ala Arg Asp Leu Gly Leu Asp Pro Gly Lys Gln Ile Lys
            500                 505                 510
Leu Asp Ser Ser Ala Gln Phe Gly Tyr Tyr Phe Arg Val Thr Cys Lys
            515                 520                 525
Glu Glu Lys Val Leu Arg Asn Asn Lys Asn Phe Ser Thr Val Asp Ile
            530                 535                 540
```

-continued

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Ala Gln Asp Ala
            565                 570                 575

Ile Val Lys Glu Ile Val Asn Ile Ser Ser Gly Tyr Val Glu Pro Met
                580                 585                 590

Gln Thr Leu Asn Asp Val Leu Ala Gln Leu Asp Ala Val Val Ser Phe
            595                 600                 605

Ala His Val Ser Asn Gly Ala Pro Val Pro Tyr Val Arg Pro Ala Ile
    610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
            675                 680                 685

Ala Gln Ile Gly Cys Phe Val Pro Cys Glu Ser Ala Glu Val Ser Ile
690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Asp Glu Leu Gly Arg
            740                 745                 750

Gly Thr Ser Thr Tyr Asp Gly Phe Gly Leu Ala Trp Ala Ile Ser Glu
            755                 760                 765

Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
            835                 840                 845

Leu Glu Leu Glu Glu Phe Gln Tyr Ile Gly Glu Ser Gln Gly Tyr Asp
850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
            900                 905                 910

Ala Glu Val Ile Ala Lys Asn Asn Ser Phe Val Asn Glu Ile Ile Ser
            915                 920                 925

Arg Ile Lys Val Thr Thr
    930

<210> SEQ ID NO 18
<211> LENGTH: 1068

```
<212> TYPE: PRT
<213> ORGANISM: Homo sapiens

<400> SEQUENCE: 18

Met Ser Arg Gln Ser Thr Leu Tyr Ser Phe Phe Pro Lys Ser Pro Ala
1               5                   10                  15

Leu Ser Asp Ala Asn Lys Ala Ser Ala Arg Ala Ser Arg Glu Gly Gly
                20                  25                  30

Arg Ala Ala Ala Pro Gly Ala Ser Pro Ser Pro Gly Gly Asp Ala
        35                  40                  45

Ala Trp Ser Glu Ala Gly Pro Gly Pro Arg Pro Leu Ala Arg Ser Ala
    50                  55                  60

Ser Pro Pro Lys Ala Lys Asn Leu Asn Gly Gly Leu Arg Arg Ser Val
65                  70                  75                  80

Ala Pro Ala Ala Pro Thr Ser Cys Asp Phe Ser Pro Gly Asp Leu Val
                85                  90                  95

Trp Ala Lys Met Glu Gly Tyr Pro Trp Trp Pro Cys Leu Val Tyr Asn
                100                 105                 110

His Pro Phe Asp Gly Thr Phe Ile Arg Glu Lys Gly Lys Ser Val Arg
            115                 120                 125

Val His Val Gln Phe Phe Asp Asp Ser Pro Thr Arg Gly Trp Val Ser
    130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Met
    195                 200                 205

Glu Val Gly Thr Thr Tyr Val Thr Asp Lys Ser Glu Glu Asp Asn Glu
210                 215                 220

Ile Glu Ser Glu Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255

Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Arg Met Val
    290                 295                 300

Thr Gly Asn Gly Ser Leu Lys Arg Lys Ser Arg Lys Glu Thr Pro
305                 310                 315                 320

Ser Ala Thr Lys Gln Ala Thr Ser Ile Ser Ser Glu Thr Lys Asn Thr
                325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
        355                 360                 365

Thr Leu Glu Trp Leu Lys Glu Glu Lys Arg Arg Asp Glu His Arg Arg
370                 375                 380

Arg Pro Asp His Pro Asp Phe Asp Ala Ser Thr Leu Tyr Val Pro Glu
385                 390                 395                 400
```

-continued

```
Asp Phe Leu Asn Ser Cys Thr Pro Gly Met Arg Lys Trp Trp Gln Ile
                405                 410                 415

Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
        435                 440                 445

Leu Val Phe Met Lys Gly Asn Trp Ala His Ser Gly Phe Pro Glu Ile
    450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
                485                 490                 495

Arg Lys Met Ala His Ile Ser Lys Tyr Asp Arg Val Val Arg Arg Glu
            500                 505                 510

Ile Cys Arg Ile Ile Thr Lys Gly Thr Gln Thr Tyr Ser Val Leu Glu
        515                 520                 525

Gly Asp Pro Ser Glu Asn Tyr Ser Lys Tyr Leu Leu Ser Leu Lys Glu
    530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
                565                 570                 575

Arg His Cys Ser Arg Phe Arg Thr Leu Val Ala His Tyr Pro Pro Val
            580                 585                 590

Gln Val Leu Phe Glu Lys Gly Asn Leu Ser Lys Glu Thr Lys Thr Ile
        595                 600                 605

Leu Lys Ser Ser Leu Ser Cys Ser Leu Gln Glu Gly Leu Ile Pro Gly
    610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
            660                 665                 670

Pro Gly Glu Lys Ser Glu Leu Ala Leu Ser Ala Leu Gly Gly Cys Val
        675                 680                 685

Phe Tyr Leu Lys Lys Cys Leu Ile Asp Gln Glu Leu Leu Ser Met Ala
    690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
                725                 730                 735

Ala Val Thr Leu Asn Asn Leu Glu Ile Phe Leu Asn Gly Thr Asn Gly
            740                 745                 750

Ser Thr Glu Gly Thr Leu Leu Glu Arg Val Asp Thr Cys His Thr Pro
        755                 760                 765

Phe Gly Lys Arg Leu Leu Lys Gln Trp Leu Cys Ala Pro Leu Cys Asn
    770                 775                 780

His Tyr Ala Ile Asn Asp Arg Leu Asp Ala Ile Glu Asp Leu Met Val
785                 790                 795                 800

Val Pro Asp Lys Ile Ser Glu Val Val Glu Leu Leu Lys Lys Leu Pro
                805                 810                 815
```

-continued

```
Asp Leu Glu Arg Leu Leu Ser Lys Ile His Asn Val Gly Ser Pro Leu
            820                 825                 830

Lys Ser Gln Asn His Pro Asp Ser Arg Ala Ile Met Tyr Glu Glu Thr
        835                 840                 845

Thr Tyr Ser Lys Lys Lys Ile Ile Asp Phe Leu Ser Ala Leu Glu Gly
    850                 855                 860

Phe Lys Val Met Cys Lys Ile Ile Gly Ile Met Glu Glu Val Ala Asp
865                 870                 875                 880

Gly Phe Lys Ser Lys Ile Leu Lys Gln Val Ile Ser Leu Gln Thr Lys
                885                 890                 895

Asn Pro Glu Gly Arg Phe Pro Asp Leu Thr Val Glu Leu Asn Arg Trp
            900                 905                 910

Asp Thr Ala Phe Asp His Glu Lys Ala Arg Lys Thr Gly Leu Ile Thr
        915                 920                 925

Pro Lys Ala Gly Phe Asp Ser Asp Tyr Asp Gln Ala Leu Ala Asp Ile
    930                 935                 940

Arg Glu Asn Glu Gln Ser Leu Leu Glu Tyr Leu Glu Lys Gln Arg Asn
945                 950                 955                 960

Arg Ile Gly Cys Arg Thr Ile Val Tyr Trp Gly Ile Gly Arg Asn Arg
                965                 970                 975

Tyr Gln Leu Glu Ile Pro Glu Asn Phe Thr Thr Arg Asn Leu Pro Glu
            980                 985                 990

Glu Tyr Glu Leu Lys Ser Thr Lys  Lys Gly Cys Lys Arg  Tyr Trp Thr
        995                 1000                1005

Lys Thr Ile Glu Lys Lys Leu Ala Asn Leu Ile Asn Ala Glu Glu
    1010                1015                 1020

Arg Arg Asp Val Ser Leu Lys Asp Cys Met Arg Arg  Leu Phe Tyr
    1025                1030                1035

Asn Phe Asp Lys Asn Tyr Lys  Asp Trp Gln Ser Ala  Val Glu Cys
    1040                1045                1050

Ile Ala Val Leu Asp Val Leu  Leu Cys Leu Ala Asn  Tyr Ser Arg
    1055                1060                1065
```